US010159571B2

(12) United States Patent
de Canniere et al.

(10) Patent No.: US 10,159,571 B2
(45) Date of Patent: Dec. 25, 2018

(54) DEVICE AND METHOD OF TREATING HEART VALVE MALFUNCTION

(71) Applicant: CorQuest Medical, Inc., Mont-Saint-Guibert (BE)

(72) Inventors: Didier de Canniere, Miami Beach, FL (US); Christophe Moureaux, Besancon (FR)

(73) Assignee: CorQuest Medical, Inc., Mont-Saint-Guibert (BE)

( * ) Notice: Subject to any disclaimer, the term of this patent is extended or adjusted under 35 U.S.C. 154(b) by 196 days.

(21) Appl. No.: 13/967,647

(22) Filed: Aug. 15, 2013

(65) Prior Publication Data
US 2014/0142687 A1 May 22, 2014

Related U.S. Application Data

(63) Continuation-in-part of application No. 13/691,087, filed on Nov. 30, 2012, now abandoned.
(Continued)

(51) Int. Cl.
*A61F 2/24* (2006.01)
*A61B 17/04* (2006.01)
(Continued)

(52) U.S. Cl.
CPC ........ *A61F 2/2466* (2013.01); *A61B 17/0401* (2013.01); *A61B 17/068* (2013.01);
(Continued)

(58) Field of Classification Search
CPC .... A61F 2/2427; A61F 2/2457; A61F 2/2466; A61B 2017/0496; A61B 17/068;
(Continued)

(56) References Cited

U.S. PATENT DOCUMENTS 3,587,567 A 6/1971 Schiff
4,536,893 A 8/1985 Parravicini
(Continued)

FOREIGN PATENT DOCUMENTS

EP 0577400 B1 10/1999
EP 1147743 10/2001
(Continued)

OTHER PUBLICATIONS

Mike Blaber, Metals, Non-Metals, and Metalloids, http://www.mikeblaber.org/oldwine/chm 1045/notes/Periodic/Metals/Period06.htm, 1996, accessed May 14, 2015.

*Primary Examiner* — Robert Lynch
(74) *Attorney, Agent, or Firm* — Wolf, Greenfield & Sacks, P.C.

(57) ABSTRACT

An assembly and method for treating heart valve malfunction including mitral regurgitation wherein an elongated chord is movably disposed within an introductory sheath and an anchor is secured to a distal end thereof. The sheath and the chord are introduced into the heart chamber and penetrate and pass through the anterior mitral valve leaflet and preferably through the mitral valve orifice. The sheath and the chord are then extended transversely across the heart chamber and the distal end of the chord is anchored to an opposing portion of the heart wall. The sheath is withdrawn back along the length of the anchored chord through the anterior mitral valve leaflet and the proximal end of the chord is secured to the valve leaflet. The chord is secured under sufficient tension to maintain an intended positioning of the valve leaflet to overcome mitral regurgitation.

12 Claims, 15 Drawing Sheets

Related U.S. Application Data

(60) Provisional application No. 61/729,152, filed on Nov. 21, 2012.

(51) Int. Cl.
*A61B 17/064* (2006.01)
*A61B 17/068* (2006.01)

(52) U.S. Cl.
CPC ........ *A61B 17/0643* (2013.01); *A61F 2/2457* (2013.01); *A61B 17/0482* (2013.01); *A61B 2017/045* (2013.01); *A61B 2017/0409* (2013.01); *A61B 2017/0437* (2013.01); *A61B 2017/0464* (2013.01)

(58) Field of Classification Search
CPC ............ A61B 17/0401; A61B 17/0643; A61B 17/0482; A61B 17/0487; A61B 2017/0409; A61B 2017/045; A61B 2017/0437; A61B 2017/0464; A61B 2017/0488; A61B 2017/049; A61B 2017/0414; A61B 2017/0419
USPC .................. 606/220, 221, 224; 623/2.1, 2.11
See application file for complete search history.

(56) References Cited

U.S. PATENT DOCUMENTS

| | | | |
|---|---|---|---|
| 4,690,134 A | 9/1987 | Snyders | |
| 5,201,742 A | 4/1993 | Hasson | |
| 5,591,170 A | 1/1997 | Spievack et al. | |
| 5,702,421 A | 12/1997 | Schneidt | |
| 6,063,070 A | 5/2000 | Eder | |
| 6,206,907 B1 | 3/2001 | Marino et al. | |
| 6,328,757 B1 | 12/2001 | Matheny | |
| 6,425,911 B1 | 7/2002 | Akerfeldt et al. | |
| 6,508,828 B1 | 1/2003 | Akerfeldt et al. | |
| 6,537,290 B2 | 3/2003 | Adams et al. | |
| 6,596,012 B2 | 7/2003 | Akerfeldt et al. | |
| 6,616,596 B1 | 9/2003 | Milbocker | |
| 6,641,592 B1* | 11/2003 | Sauer ................. A61B 17/0057 606/144 |
| 6,682,489 B2 | 1/2004 | Tenerz et al. | |
| 6,712,837 B2 | 3/2004 | Akerfeldt et al. | |
| 6,902,522 B1 | 6/2005 | Walsh | |
| 6,929,655 B2 | 8/2005 | Egnelöv et al. | |
| 6,960,220 B2 | 11/2005 | Marino et al. | |
| 7,044,916 B2 | 5/2006 | Tenerz et al. | |
| 7,445,626 B2* | 11/2008 | Songer ............... A61B 17/0057 606/224 |
| 8,092,363 B2 | 1/2012 | Leinsing | |
| 8,133,168 B2 | 3/2012 | Monnet | |
| 8,147,542 B2 | 4/2012 | Maisano et al. | |
| 8,408,214 B2 | 4/2013 | Spenser | |
| 8,506,624 B2 | 8/2013 | Vidlund | |
| 8,758,393 B2 | 6/2014 | Zentgraf | |
| 8,790,394 B2 | 7/2014 | Miller | |
| 9,566,443 B2 | 2/2017 | de Canniere | |
| 2002/0100485 A1 | 8/2002 | Stevens et al. | |
| 2002/0161378 A1 | 10/2002 | Downing | |
| 2003/0120337 A1 | 6/2003 | Van Tassel et al. | |
| 2004/0087831 A1 | 5/2004 | Michels et al. | |
| 2004/0102804 A1 | 5/2004 | Chin | |
| 2004/0106945 A1 | 6/2004 | Thramann et al. | |
| 2004/0116897 A1 | 6/2004 | Aboul-Hosn | |
| 2004/0138526 A1 | 7/2004 | Guenst | |
| 2005/0137700 A1* | 6/2005 | Spence ............... A61B 17/0401 623/2.36 |
| 2005/0149108 A1 | 7/2005 | Cox | |
| 2006/0074484 A1 | 4/2006 | Huber | |
| 2006/0135962 A1 | 6/2006 | Kick et al. | |
| 2006/0241655 A1* | 10/2006 | Viola ................. A61B 17/128 606/142 |
| 2006/0247672 A1 | 11/2006 | Vidlund et al. | |
| 2007/0055206 A1* | 3/2007 | To ..................... A61B 17/0401 604/191 |
| 2007/0135826 A1 | 6/2007 | Zaver et al. | |
| 2007/0162066 A1 | 7/2007 | Lyon | |
| 2007/0239108 A1 | 10/2007 | Albrecht et al. | |
| 2007/0265643 A1 | 11/2007 | Beane et al. | |
| 2008/0033241 A1 | 2/2008 | Peh et al. | |
| 2008/0114342 A1 | 5/2008 | Whayne et al. | |
| 2008/0140116 A1* | 6/2008 | Bonutti ............. A61B 17/0401 606/232 |
| 2008/0275295 A1 | 11/2008 | Gertner | |
| 2009/0005800 A1 | 1/2009 | Franer | |
| 2009/0105751 A1* | 4/2009 | Zentgraf ............ A61B 17/0469 606/206 |
| 2009/0192598 A1 | 7/2009 | Lattouf | |
| 2010/0042147 A1* | 2/2010 | Janovsky ........... A61B 17/0401 606/228 |
| 2010/0161042 A1 | 6/2010 | Maisano et al. | |
| 2010/0161043 A1* | 6/2010 | Maisano ............ A61B 17/0401 623/2.11 |
| 2010/0179574 A1 | 7/2010 | Longoria et al. | |
| 2010/0228077 A1 | 9/2010 | Lenker et al. | |
| 2010/0274091 A1 | 10/2010 | Rothstein et al. | |
| 2011/0029071 A1 | 2/2011 | Zlotnick et al. | |
| 2011/0060182 A1 | 3/2011 | Kassab et al. | |
| 2011/0166413 A1 | 7/2011 | Alferness | |
| 2011/0190811 A1 | 8/2011 | Shanley | |
| 2012/0276928 A1 | 1/2012 | Shutter | |
| 2012/0143209 A1 | 6/2012 | Brecheen et al. | |
| 2012/0272452 A1 | 11/2012 | Schultz | |
| 2012/0272495 A1 | 11/2012 | Hildebrandt et al. | |
| 2012/0272497 A1 | 11/2012 | Smith | |
| 2012/0272499 A1 | 11/2012 | Schley et al. | |
| 2012/0272523 A1 | 11/2012 | Calla et al. | |
| 2012/0272555 A1 | 11/2012 | Heath | |
| 2012/0272556 A1 | 11/2012 | Brown | |
| 2012/0272595 A1 | 11/2012 | Gallant | |
| 2012/0272603 A1 | 11/2012 | Carbines | |
| 2012/0272611 A1 | 11/2012 | Tsukimoto et al. | |
| 2012/0272624 A1 | 11/2012 | Argeriou et al. | |
| 2012/0272632 A1 | 11/2012 | Lans | |
| 2012/0272637 A1 | 11/2012 | Holland et al. | |
| 2012/0272652 A1 | 11/2012 | Nicholls et al. | |
| 2012/0272653 A1 | 11/2012 | Merrill et al. | |
| 2012/0272660 A1 | 11/2012 | Garrett | |
| 2012/0272661 A1 | 11/2012 | Milburn | |
| 2012/0272662 A1 | 11/2012 | Milburn | |
| 2012/0272667 A1 | 11/2012 | Ferraro et al. | |
| 2012/0272670 A1 | 11/2012 | Choi et al. | |
| 2012/0272705 A1 | 11/2012 | Hlrane | |
| 2012/0272738 A1 | 11/2012 | Klessel et al. | |
| 2012/0272741 A1 | 11/2012 | Xiao et al. | |
| 2012/0272768 A1 | 11/2012 | Schmidt et al. | |
| 2012/0272780 A1 | 11/2012 | Schimings et al. | |
| 2012/0272815 A1 | 11/2012 | Lingel et al. | |
| 2012/0272817 A1 | 11/2012 | Lindh, Sr. et al. | |
| 2012/0272841 A1 | 11/2012 | Heymanns et al. | |
| 2012/0272843 A1 | 11/2012 | Graff | |
| 2012/0272845 A1 | 11/2012 | Loiret-Bernal et al. | |
| 2012/0272846 A1 | 11/2012 | Fleischer et al. | |
| 2012/0272876 A1 | 11/2012 | Bergeron et al. | |
| 2012/0272893 A1 | 11/2012 | Lauerhaas et al. | |
| 2012/0272968 A1 | 11/2012 | Kirschner | |
| 2012/0272996 A1 | 11/2012 | Jimenez et al. | |
| 2012/0273014 A1 | 11/2012 | Tadayon | |
| 2012/0273064 A1 | 11/2012 | Ismert et al. | |
| 2012/0273078 A1 | 11/2012 | Hawwa et al. | |
| 2012/0273079 A1 | 11/2012 | Guclucan | |
| 2012/0273141 A1 | 11/2012 | Miller et al. | |
| 2012/0273142 A1 | 11/2012 | Miller et al. | |
| 2012/0273143 A1 | 11/2012 | Fillmore et al. | |
| 2012/0273161 A1 | 11/2012 | Raver | |
| 2012/0273174 A1 | 11/2012 | Barnes | |
| 2012/0273178 A1 | 11/2012 | Wanni et al. | |
| 2012/0273209 A1 | 11/2012 | Austin et al. | |
| 2012/0273210 A1 | 11/2012 | Arizmendi, Jr. et al. | |
| 2012/0273214 A1 | 11/2012 | Donald et al. | |
| 2012/0273219 A1 | 11/2012 | Hoffman et al. | |
| 2012/0273220 A1 | 11/2012 | Ezekiel et al. | |

(56) References Cited

U.S. PATENT DOCUMENTS

| | | |
|---|---|---|
| 2012/0273228 A1 | 11/2012 | Allouche |
| 2012/0273230 A1 | 11/2012 | Patterson et al. |
| 2012/0273231 A1 | 11/2012 | Whiddon |
| 2012/0273232 A1 | 11/2012 | O'Blenes |
| 2012/0273328 A1 | 11/2012 | Sejourne |
| 2012/0273358 A1 | 11/2012 | Larnoy et al. |
| 2012/0273389 A1 | 11/2012 | Aziz et al. |
| 2012/0273399 A1 | 11/2012 | Daboub et al. |
| 2012/0273438 A1 | 11/2012 | Nordin et al. |
| 2012/0273439 A1 | 11/2012 | Beavers et al. |
| 2012/0273458 A1 | 11/2012 | Bret et al. |
| 2012/0273467 A1 | 11/2012 | Baxter et al. |
| 2012/0273470 A1 | 11/2012 | Zediker et al. |
| 2012/0273513 A1 | 11/2012 | Greer, Jr. |
| 2012/0273555 A1 | 11/2012 | Flak et al. |
| 2012/0273580 A1 | 11/2012 | Warren et al. |
| 2012/0273641 A1 | 11/2012 | Gorman et al. |
| 2012/0273647 A1 | 11/2012 | Moruzzi |
| 2012/0273680 A1 | 11/2012 | Furry |
| 2012/0273843 A1 | 11/2012 | Kim |
| 2012/0273860 A1 | 11/2012 | Chen et al. |
| 2012/0273880 A1 | 11/2012 | Tenet et al. |
| 2012/0273902 A1 | 11/2012 | Lin et al. |
| 2012/0273955 A1 | 11/2012 | Or-Bach et al. |
| 2012/0273987 A1 | 11/2012 | Belcher et al. |
| 2012/0273989 A1 | 11/2012 | Graf |
| 2012/0273993 A1 | 11/2012 | Shoseyov et al. |
| 2012/0274001 A1 | 11/2012 | Prabhu |
| 2012/0274020 A1 | 11/2012 | Daboub |
| 2012/0274061 A1 | 11/2012 | Wilkinson |
| 2012/0274065 A1 | 11/2012 | Knapp |
| 2012/0274066 A1 | 11/2012 | Hanbeck |
| 2012/0274076 A1 | 11/2012 | Kelaiditis et al. |
| 2012/0274145 A1 | 11/2012 | Taddeo |
| 2012/0274198 A1 | 11/2012 | Jenek |
| 2012/0274202 A1 | 11/2012 | Komatsu |
| 2012/0274212 A1 | 11/2012 | Yu et al. |
| 2012/0274256 A1 | 11/2012 | O'Rourke |
| 2012/0274266 A1 | 11/2012 | Yip |
| 2012/0274279 A1 | 11/2012 | Banos et al. |
| 2012/0274280 A1 | 11/2012 | Yip et al. |
| 2012/0274281 A1 | 11/2012 | Kim |
| 2012/0274288 A1 | 11/2012 | Wegener |
| 2012/0274332 A1 | 11/2012 | Sinha et al. |
| 2012/0274391 A1 | 11/2012 | Kim |
| 2012/0274395 A1 | 11/2012 | Deam |
| 2012/0274440 A1 | 11/2012 | Meadows et al. |
| 2012/0274470 A1 | 11/2012 | Sandvick |
| 2012/0274477 A1 | 11/2012 | Prammer |
| 2012/0274769 A1 | 11/2012 | Lee |
| 2012/0274770 A1 | 11/2012 | Lee |
| 2012/0274772 A1 | 11/2012 | Fosburgh et al. |
| 2012/0274870 A1 | 11/2012 | Liu |
| 2012/0274937 A1 | 11/2012 | Hays et al. |
| 2012/0274962 A1 | 11/2012 | Thomas et al. |
| 2012/0275056 A1 | 11/2012 | McGuire, Jr. |
| 2012/0275057 A1 | 11/2012 | McGuire, Jr. |
| 2012/0275085 A1 | 11/2012 | Wilson et al. |
| 2012/0275128 A1 | 11/2012 | Takada et al. |
| 2012/0275140 A1 | 11/2012 | Feinbloom et al. |
| 2012/0275236 A1 | 11/2012 | Hess et al. |
| 2012/0275244 A1 | 11/2012 | Do |
| 2012/0275247 A1 | 11/2012 | Hwang et al. |
| 2012/0275248 A1 | 11/2012 | Won |
| 2012/0275249 A1 | 11/2012 | Yang et al. |
| 2012/0275298 A1 | 11/2012 | Bryant et al. |
| 2012/0275299 A1 | 11/2012 | Taylor et al. |
| 2012/0275338 A1 | 11/2012 | Filsfils et al. |
| 2012/0275356 A1 | 11/2012 | Aharony et al. |
| 2012/0275670 A1 | 11/2012 | Joglekar |
| 2012/0275754 A1 | 11/2012 | Krampotich et al. |
| 2012/0275841 A1 | 11/2012 | Jimenez et al. |
| 2012/0275843 A1 | 11/2012 | Jimenez et al. |
| 2012/0275845 A1 | 11/2012 | Etling |
| 2012/0275860 A1 | 11/2012 | Exline |
| 2012/0275861 A1 | 11/2012 | Myslowski et al. |
| 2012/0275862 A1 | 11/2012 | Vitale |
| 2012/0275881 A1 | 11/2012 | Mueller |
| 2012/0275913 A1 | 11/2012 | Robertson, Jr. et al. |
| 2012/0275924 A1 | 11/2012 | Perkinson |
| 2012/0275927 A1 | 11/2012 | Rhin |
| 2012/0275970 A1 | 11/2012 | Nash et al. |
| 2012/0275999 A1 | 11/2012 | Bell et al. |
| 2012/0276005 A1 | 11/2012 | Yang et al. |
| 2012/0276008 A1 | 11/2012 | Walkenhorst et al. |
| 2012/0276009 A1 | 11/2012 | Pfeifer et al. |
| 2012/0276011 A1 | 11/2012 | Kupussamy et al. |
| 2012/0276021 A1 | 11/2012 | Kumar et al. |
| 2012/0276025 A1 | 11/2012 | Florence et al. |
| 2012/0276041 A1 | 11/2012 | Salamone et al. |
| 2012/0276053 A1 | 11/2012 | Kim |
| 2012/0276061 A1 | 11/2012 | Grazia et al. |
| 2012/0276062 A1 | 11/2012 | Kellar et al. |
| 2012/0276064 A1 | 11/2012 | Blau et al. |
| 2012/0276067 A1 | 11/2012 | Westenfelder |
| 2012/0276068 A1 | 11/2012 | Sabaawy |
| 2012/0276069 A1 | 11/2012 | Karperien et al. |
| 2012/0276071 A1 | 11/2012 | Fraser, Jr. |
| 2012/0276073 A1 | 11/2012 | Schachner et al. |
| 2012/0276074 A1 | 11/2012 | Scharenberg et al. |
| 2012/0276080 A1 | 11/2012 | Kinoshita et al. |
| 2012/0276084 A1 | 11/2012 | Schaumberg et al. |
| 2012/0276087 A1 | 11/2012 | Schafer et al. |
| 2012/0276088 A1 | 11/2012 | El-Deiry et al. |
| 2012/0276089 A1 | 11/2012 | Lee et al. |
| 2012/0276101 A1 | 11/2012 | Kwak et al. |
| 2012/0276103 A1 | 11/2012 | Karperien et al. |
| 2012/0276104 A1 | 11/2012 | Woisetschlager |
| 2012/0276110 A1 | 11/2012 | Simard |
| 2012/0276111 A1 | 11/2012 | Hafezi-Moghadam |
| 2012/0276126 A1 | 11/2012 | Varadhachary et al. |
| 2012/0276130 A1 | 11/2012 | Margarit Y Ros et al. |
| 2012/0276139 A1 | 11/2012 | Moormann et al. |
| 2012/0276143 A1 | 11/2012 | O'Mahony et al. |
| 2012/0276144 A1 | 11/2012 | Kernodle et al. |
| 2012/0276149 A1 | 11/2012 | Littman et al. |
| 2012/0276150 A1 | 11/2012 | Lauritzen et al. |
| 2012/0276151 A1 | 11/2012 | Lewis et al. |
| 2012/0276152 A1 | 11/2012 | Hossainy et al. |
| 2012/0276161 A1 | 11/2012 | Gravagna et al. |
| 2012/0276164 A1 | 11/2012 | Tuominen et al. |
| 2012/0276169 A1 | 11/2012 | Kang et al. |
| 2012/0276173 A1 | 11/2012 | Marcum et al. |
| 2012/0276182 A1 | 11/2012 | Baker, Jr. et al. |
| 2012/0276185 A1 | 11/2012 | Hossainy et al. |
| 2012/0276188 A1 | 11/2012 | Barrows |
| 2012/0276189 A1 | 11/2012 | Johnson |
| 2012/0276193 A1 | 11/2012 | Graversen et al. |
| 2012/0276201 A1 | 11/2012 | Trachtman |
| 2012/0276202 A1 | 11/2012 | Selim et al. |
| 2012/0276203 A1 | 11/2012 | Selim et al. |
| 2012/0276204 A1 | 11/2012 | Remington et al. |
| 2012/0276213 A1 | 11/2012 | Chen |
| 2012/0276218 A1 | 11/2012 | Jung et al. |
| 2012/0276232 A1 | 11/2012 | Marczyk et al. |
| 2012/0276237 A1 | 11/2012 | Heymanns et al. |
| 2012/0276278 A1 | 11/2012 | Qiu et al. |
| 2012/0276286 A1 | 11/2012 | Vijayakumar |
| 2012/0276296 A1 | 11/2012 | Fieberg et al. |
| 2012/0276297 A1 | 11/2012 | Cypcar et al. |
| 2012/0276304 A1 | 11/2012 | Derrien |
| 2012/0276330 A1 | 11/2012 | Durney et al. |
| 2012/0276365 A1 | 11/2012 | Petuskey et al. |
| 2012/0276375 A1 | 11/2012 | Colgan et al. |
| 2012/0276381 A1 | 11/2012 | Cypcar |
| 2012/0276427 A1 | 11/2012 | Kim |
| 2012/0276463 A1 | 11/2012 | Grannell et al. |
| 2012/0276465 A1 | 11/2012 | Paganelli |
| 2012/0276469 A1 | 11/2012 | Shizuku |
| 2012/0276509 A1 | 11/2012 | Iannotti et al. |
| 2012/0276518 A1 | 11/2012 | Gillis |
| 2012/0276522 A1 | 11/2012 | Huang et al. |
| 2012/0276528 A1 | 11/2012 | Cargill et al. |
| 2012/0276529 A1 | 11/2012 | Galisson et al. |

(56) References Cited

U.S. PATENT DOCUMENTS

| | | |
|---|---|---|
| 2012/0276537 A1 | 11/2012 | Kühn et al. |
| 2012/0276552 A1 | 11/2012 | Lu |
| 2012/0276553 A1 | 11/2012 | Gronthoe et al. |
| 2012/0276554 A1 | 11/2012 | Gutteridge et al. |
| 2012/0276555 A1 | 11/2012 | Kuhn et al. |
| 2012/0276558 A1 | 11/2012 | Soper et al. |
| 2012/0276572 A1 | 11/2012 | Shekdar et al. |
| 2012/0276581 A1 | 11/2012 | Arav et al. |
| 2012/0276588 A1 | 11/2012 | Hallen-Adams et al. |
| 2012/0276591 A1 | 11/2012 | Kneissel et al. |
| 2012/0276618 A1 | 11/2012 | Dayton et al. |
| 2012/0276626 A1 | 11/2012 | Shogbon et al. |
| 2012/0276627 A1 | 11/2012 | Kelnar et al. |
| 2012/0276628 A1 | 11/2012 | Khan et al. |
| 2012/0276632 A1 | 11/2012 | Strunk et al. |
| 2012/0276679 A1 | 11/2012 | Wu |
| 2012/0276694 A1 | 11/2012 | Koezuka et al. |
| 2012/0276754 A1 | 11/2012 | Cordingley et al. |
| 2012/0276887 A1 | 11/2012 | Romine et al. |
| 2012/0277006 A1 | 11/2012 | Kim |
| 2012/0277008 A1 | 11/2012 | Kitchen et al. |
| 2012/0277051 A1 | 11/2012 | Cooper et al. |
| 2012/0277073 A1 | 11/2012 | Bartsch |
| 2012/0277093 A1 | 11/2012 | Andrew et al. |
| 2012/0277110 A1 | 11/2012 | Andre et al. |
| 2012/0277111 A1 | 11/2012 | Crabtree et al. |
| 2012/0277112 A1 | 11/2012 | Linn et al. |
| 2012/0277118 A1 | 11/2012 | Bhati et al. |
| 2012/0277120 A1 | 11/2012 | Serber et al. |
| 2012/0277144 A1 | 11/2012 | Duckers |
| 2012/0277152 A1 | 11/2012 | Ringeisen et al. |
| 2012/0277155 A1 | 11/2012 | VanAntwerp et al. |
| 2012/0277156 A1 | 11/2012 | Gross et al. |
| 2012/0277157 A1 | 11/2012 | Hillman |
| 2012/0277161 A1 | 11/2012 | Agrez et al. |
| 2012/0277162 A1 | 11/2012 | Krasnoperov et al. |
| 2012/0277173 A1 | 11/2012 | Eidenberger |
| 2012/0277179 A1 | 11/2012 | Bhargava |
| 2012/0277195 A1 | 11/2012 | Banov et al. |
| 2012/0277203 A1 | 11/2012 | Lasley et al. |
| 2012/0277204 A1 | 11/2012 | Taniguchi et al. |
| 2012/0277205 A1 | 11/2012 | Badorc et al. |
| 2012/0277210 A1 | 11/2012 | Catron et al. |
| 2012/0277215 A1 | 11/2012 | Ksander et al. |
| 2012/0277228 A1 | 11/2012 | Sutton et al. |
| 2012/0277229 A1 | 11/2012 | Bearss et al. |
| 2012/0277251 A1 | 11/2012 | Palladino et al. |
| 2012/0277265 A1 | 11/2012 | Deraeve et al. |
| 2012/0277269 A1 | 11/2012 | Reilly |
| 2012/0277271 A1 | 11/2012 | Nadeson et al. |
| 2012/0277277 A1 | 11/2012 | Wallace et al. |
| 2012/0277279 A1 | 11/2012 | Barnett et al. |
| 2012/0277282 A1 | 11/2012 | Gotthardt et al. |
| 2012/0277288 A1 | 11/2012 | Drumm et al. |
| 2012/0277307 A1 | 11/2012 | Waddell |
| 2012/0277309 A1 | 11/2012 | Severa et al. |
| 2012/0277312 A1 | 11/2012 | Mink et al. |
| 2012/0277316 A1 | 11/2012 | Tillman et al. |
| 2012/0277319 A1 | 11/2012 | Steigerwald et al. |
| 2012/0277324 A1 | 11/2012 | Burk et al. |
| 2012/0277364 A1 | 11/2012 | Lolli et al. |
| 2012/0277376 A1 | 11/2012 | Baker, Jr. et al. |
| 2012/0277382 A1 | 11/2012 | Booth et al. |
| 2012/0277412 A1 | 11/2012 | Furusako et al. |
| 2012/0277430 A1 | 11/2012 | Taniguchi et al. |
| 2012/0277431 A1 | 11/2012 | Taniguchi et al. |
| 2012/0277451 A1 | 11/2012 | Ochiai |
| 2012/0277453 A1 | 11/2012 | Franklin et al. |
| 2012/0277517 A1 | 11/2012 | Ivkov et al. |
| 2012/0277521 A1 | 11/2012 | Chamberlin |
| 2012/0277522 A1 | 11/2012 | Shalon et al. |
| 2012/0277523 A1 | 11/2012 | Shalon et al. |
| 2012/0277537 A1 | 11/2012 | Kucklick et al. |
| 2012/0277544 A1 | 11/2012 | Fernandes et al. |
| 2012/0277546 A1 | 11/2012 | Soykan et al. |
| 2012/0277567 A1 | 11/2012 | Harlev et al. |
| 2012/0277572 A1 | 11/2012 | Hubbard |
| 2012/0277574 A1 | 11/2012 | Panescu |
| 2012/0277576 A1 | 11/2012 | Lui |
| 2012/0277578 A1 | 11/2012 | Gunday et al. |
| 2012/0277582 A1 | 11/2012 | Mafi |
| 2012/0277584 A1 | 11/2012 | Tanaka et al. |
| 2012/0277592 A1 | 11/2012 | Zelenka et al. |
| 2012/0277599 A1 | 11/2012 | Greenhut |
| 2012/0277600 A1 | 11/2012 | Greenhut |
| 2012/0277618 A1 | 11/2012 | Giftakis et al. |
| 2012/0277621 A1 | 11/2012 | Gerber et al. |
| 2012/0277624 A1 | 11/2012 | Cucin |
| 2012/0277626 A1 | 11/2012 | Burbank et al. |
| 2012/0277638 A1 | 11/2012 | Skelton et al. |
| 2012/0277639 A1 | 11/2012 | Pollock et al. |
| 2012/0277642 A1 | 11/2012 | Smith et al. |
| 2012/0277668 A1 | 11/2012 | Chawla |
| 2012/0277671 A1 | 11/2012 | Fuentes |
| 2012/0277672 A1 | 11/2012 | Pepper et al. |
| 2012/0277674 A1 | 11/2012 | Clark, III et al. |
| 2012/0277693 A1 | 11/2012 | Bailey |
| 2012/0277716 A1 | 11/2012 | Ali et al. |
| 2012/0277718 A1 | 11/2012 | Campbell et al. |
| 2012/0277720 A1 | 11/2012 | Humes et al. |
| 2012/0277725 A1 | 11/2012 | Kassab et al. |
| 2012/0277729 A1 | 11/2012 | Melsheimer |
| 2012/0277730 A1 | 11/2012 | Salahieh et al. |
| 2012/0277736 A1 | 11/2012 | Francischelli |
| 2012/0277740 A1 | 11/2012 | Wamking et al. |
| 2012/0277741 A1 | 11/2012 | Davalos et al. |
| 2012/0277743 A1 | 11/2012 | Vallittu |
| 2012/0277746 A1 | 11/2012 | Morgan et al. |
| 2012/0277749 A1 | 11/2012 | Mootien et al. |
| 2012/0277752 A1 | 11/2012 | Wasielewski |
| 2012/0277753 A1 | 11/2012 | Linderman et al. |
| 2012/0277756 A1 | 11/2012 | Ray et al. |
| 2012/0277766 A1 | 11/2012 | Ferree |
| 2012/0277770 A1 | 11/2012 | Fenton et al. |
| 2012/0277771 A1 | 11/2012 | Vaz et al. |
| 2012/0277772 A1 | 11/2012 | Aben et al. |
| 2012/0277773 A1 | 11/2012 | Sargeant et al. |
| 2012/0277774 A1 | 11/2012 | Guo |
| 2012/0277776 A1 | 11/2012 | Kraemer et al. |
| 2012/0277781 A1 | 11/2012 | Gertner |
| 2012/0277784 A1 | 11/2012 | Berez et al. |
| 2012/0277785 A1 | 11/2012 | Aggerholm et al. |
| 2012/0277786 A1 | 11/2012 | Mohl |
| 2012/0277791 A1 | 11/2012 | Abo-Auda et al. |
| 2012/0277792 A1 | 11/2012 | Teeslink et al. |
| 2012/0277793 A1 | 11/2012 | Marczyk et al. |
| 2012/0277798 A1 | 11/2012 | Benson et al. |
| 2012/0277800 A1 | 11/2012 | Jackson |
| 2012/0277807 A1 | 11/2012 | Myung et al. |
| 2012/0277811 A1 | 11/2012 | Lauchner et al. |
| 2012/0277812 A1 | 11/2012 | Kraus |
| 2012/0277814 A1 | 11/2012 | Schuler |
| 2012/0277820 A1 | 11/2012 | Wu et al. |
| 2012/0277823 A1 | 11/2012 | Gerber et al. |
| 2012/0277825 A1 | 11/2012 | Mawson et al. |
| 2012/0277833 A1 | 11/2012 | Gerber et al. |
| 2012/0277835 A1 | 11/2012 | Della Santina et al. |
| 2012/0277837 A1 | 11/2012 | Schuler |
| 2012/0277843 A1 | 11/2012 | Weber et al. |
| 2012/0277845 A1 | 11/2012 | Bowe |
| 2012/0277846 A1 | 11/2012 | Schreck et al. |
| 2012/0277852 A1 | 11/2012 | Shukla et al. |
| 2012/0277853 A1 | 11/2012 | Rothstein |
| 2012/0277854 A1 | 11/2012 | Ryan |
| 2012/0277855 A1 | 11/2012 | Lashinski et al. |
| 2012/0277856 A1 | 11/2012 | Spenser et al. |
| 2012/0277862 A1 | 11/2012 | Tornier et al. |
| 2012/0277864 A1 | 11/2012 | Brodke et al. |
| 2012/0277865 A1 | 11/2012 | Trieu et al. |
| 2012/0277867 A1 | 11/2012 | Kana et al. |
| 2012/0277872 A1 | 11/2012 | Kana et al. |
| 2012/0277873 A1 | 11/2012 | Kana et al. |
| 2012/0277879 A1 | 11/2012 | Ripamonti |
| 2012/0277880 A1 | 11/2012 | Winslow et al. |

(56) References Cited

U.S. PATENT DOCUMENTS

| | | |
|---|---|---|
| 2012/0277882 A1 | 11/2012 | Huang et al. |
| 2012/0277896 A1 | 11/2012 | Uekita et al. |
| 2012/0277903 A1 | 11/2012 | Schaefer |
| 2012/0277939 A1 | 11/2012 | Kumar |
| 2012/0277940 A1 | 11/2012 | Kumar et al. |
| 2012/0277949 A1 | 11/2012 | Ghimire et al. |
| 2012/0277979 A1 | 11/2012 | Kato et al. |
| 2012/0277998 A1 | 11/2012 | Bevilacqua et al. |
| 2012/0277999 A1 | 11/2012 | Somogyi et al. |
| 2012/0278032 A1 | 11/2012 | Chen |
| 2012/0278098 A1 | 11/2012 | Vovan et al. |
| 2012/0278099 A1 | 11/2012 | Kelly et al. |
| 2012/0278123 A1 | 11/2012 | Houle |
| 2012/0278144 A1 | 11/2012 | Popllock et al. |
| 2012/0278195 A1 | 11/2012 | Joseph |
| 2012/0278200 A1 | 11/2012 | van Coppenolle et al. |
| 2012/0278236 A1 | 11/2012 | Jain et al. |
| 2012/0278242 A1 | 11/2012 | Griffith |
| 2012/0278411 A1 | 11/2012 | Lavine |
| 2012/0278439 A1 | 11/2012 | Ahiska et al. |
| 2012/0278454 A1 | 11/2012 | Stewart et al. |
| 2012/0278484 A1 | 11/2012 | Westphal |
| 2012/0278520 A1 | 11/2012 | Barrenscheen et al. |
| 2012/0278554 A1 | 11/2012 | Eilert |
| 2012/0278592 A1 | 11/2012 | Tran |
| 2012/0278597 A1 | 11/2012 | De Atley et al. |
| 2012/0278654 A1 | 11/2012 | Shen et al. |
| 2012/0278657 A1 | 11/2012 | Baker et al. |
| 2012/0278676 A1 | 11/2012 | Teraura |
| 2012/0278684 A1 | 11/2012 | Eldredge et al. |
| 2012/0278689 A1 | 11/2012 | Tamo et al. |
| 2012/0278760 A1 | 11/2012 | Cerny et al. |
| 2012/0278771 A1 | 11/2012 | Ren |
| 2012/0278799 A1 | 11/2012 | Starks et al. |
| 2012/0278865 A1 | 11/2012 | Sawdy |
| 2012/0278913 A1 | 11/2012 | Fraser |
| 2012/0278947 A1 | 11/2012 | Guo |
| 2012/0278957 A1 | 11/2012 | Phan et al. |
| 2012/0283758 A1 | 11/2012 | Miller |
| 2013/0041395 A1 | 2/2013 | De Canniere |
| 2013/0066275 A1 | 3/2013 | De Canniere |
| 2015/0148590 A1 | 5/2015 | de Canniere |

FOREIGN PATENT DOCUMENTS

| | | |
|---|---|---|
| EP | 1169968 | 1/2002 |
| EP | 1222896 | 7/2002 |
| EP | 1266626 | 12/2002 |
| EP | 1269919 | 1/2003 |
| EP | 1254634 | 7/2003 |
| EP | 1244725 | 7/2005 |
| EP | 1773239 B1 | 3/2010 |
| WO | WO 2012 040865 | 4/2012 |
| WO | WO2012016398 A1 | 9/2012 |
| WO | WO2013/023016 | 2/2013 |
| WO | WO 2013036742 | 3/2013 |
| WO | WO2015081053 A1 | 6/2015 |

* cited by examiner

DEVICE AND METHOD OF TREATING HEART VALVE MALFUNCTION

CLAIM OF PRIORITY

The present application is a continuation in part of U.S. patent application Ser. No. 13/691,087, filed Nov. 30, 2012, which claims the benefit under 35 U.S.C. Section 119(e) of Provisional Patent Application Ser. No. 61/729,152, filed Nov. 21, 2012, and which is incorporated herein by reference in its entirety.

BACKGROUND OF THE INVENTION

Field of the Invention

The present invention is directed to an instrument assembly and method of use and application in the treatment of heart valve malfunction. In more specific terms the instrument assembly is specifically adapted to treat mitral regurgitation by means of a direct entry of the instrument through the atrial wall rather than through the vascular system, in order to apply sufficient tension to a prolapsing leaflet, including the anterior leaflet and/or the posterior leaflet of the mitral valve, in order to overcome mitral regurgitation.

Description of the Related Art

The human heart is a four chambered pump that moves blood efficiently through the vascular system. During normal operation, blood enters the heart through the vena cava and flows into the right atrium. Thereafter, blood flows from the right atrium through the tricuspid valve and into the right ventricle. Upon contraction of the right ventricle, blood is forced through the pulmonic valve and into the lungs for oxygenation. The oxygenated blood returns from the lungs and enters the heart through the left atrium and passes through the mitral valve into the left ventricle. Upon contraction of the left ventricle the blood therein flows through the aortic valve and into the aorta and throughout the vascular system.

The mitral valve is disposed in flow regulating communication between the left atrium and the left ventricle. It is composed of two valve leaflets, the mitral valve annulus, which forms a ring that supports the valve leaflets; papillary muscles, which tether the valve leaflets to the left ventricle wall, by preventing them from prolapsing back into the left atrium. Chordae tendineae serve to connect the mitral valve leaflets to the papillary muscles thereby further preventing the leaflets from prolapsing back into the left atrium. A dysfunction of any of these components of the mitral valve can cause "mitral regurgitation". Mitral regurgitation is a disorder of the heart in which the mitral valve does not close properly when the heart pumps out blood. This results in abnormal leaking of blood from the left ventricle back into the left atrium, through the mitral valve, when the left ventricle contracts and is a condition known as "mitral regurgitation". It is generally recognized in the medical profession that mitral regurgitation is the second most common form of valvular heart disease.

As generally set forth above, when properly functioning, the anterior and posterior valve leaflets of the mitral valve overlap during contraction of the left ventricle and prevent blood from flowing back into the left atrium. This overlap of the 2 leaflets leaning upon each other is called the coaptation and absorbs most of the strain on the mitral apparatus during the ventricular contraction. However, when the mitral valve malfunctions, due to various cardiac diseases, the leaflets are no longer coapting resulting in the mitral valve remaining partially open during ventricular contraction. In turn this allows the "regurgitation" of the blood back into the left atrium, as generally set forth above. When the mitral valve does not close hermetically during the ventricular contraction, the aforementioned back flow of blood to the atrium and the pulmonary vasculature, results in a deleterious condition. More specifically, this condition increases the work load to the heart and may lead to heart failure.

Methods of treating conditions relating to the malfunctioning of the heart valve specifically including valve incompetencies, mitral valve leakage and other heart failure conditions may be in various stages of development, such as the extending of an elongate member transverse across a corresponding or affected heart chamber. Each end of the elongate member extends through a wall of the heart such as the septum wall and an oppositely disposed wall portion, wherein first and second anchoring members are connected to corresponding ends of the elongate member but are disposed external of the heart chamber. Connecting clips or the like are applied to the corresponding exterior ends of the elongate member, resulting in the papillary muscles within the chamber to be effectively re-shaped or repositioned. A predetermined force is applied to the heart itself and/or the affected portions of the heart chamber.

Other specific treatments associated with mitral regurgitation sometimes may include the surgical repair or replacement of the mitral valve, resulting in traumatic and frequently dangerous surgical procedures being performed on a patient.

Accordingly, there is a need in the medical arts for appropriate instrumentation and attendant methods of overcoming heart valve malfunctions, specifically including mitral regurgitation.

SUMMARY OF THE INVENTION

The present invention is directed to an instrument assembly and attendant method for treating heart valve malfunction. In more specific terms, the instrumentation and method are specifically, but not exclusively, adapted for the treatment of mitral regurgitation. However, for purposes of clarity and in order to emphasize the versatility of the various embodiments of the present invention, the subject instrument assembly and method will be described generically regarding treatment of a predetermined heart valve. In addition, the present invention will be more specifically described in regard to a procedure involving correction of a prolapsing mitral valve leaflet, which may include the anterior mitral valve leaflet and/or the posterior valve leaflet correcting of mitral regurgitation.

Accordingly, the instrument assembly of the present invention includes an introductory sheath formed of a material of sufficient rigidity to facilitate the penetration and passage through various portions of the heart and mitral valve. As such, the introductory sheath may be said to be formed of at least a "semi-rigid" material. However, this term is to be understood to include material having sufficient flexibility to be manipulated or "steered" through and/or along a predetermined path during the delivery of the sheath and associated components of the instrument assembly to predetermined portions of the heart. Moreover, in one preferred embodiment the sheath will be sufficiently maneuverable to pass through the atrial wall into interior portions of the heart such as the left atrium and left ventricle. In addition and as described in greater detail hereinafter, an introduction assembly and a delivery catheter will be used to facilitate the positioning the introductory sheath into the thoracic cavity and through the atrial wall or other preferred exterior locations of the heart wall.

Additional structural operative features of the instrument assembly include the provision and utilization of at least one, or under required circumstances, more than one elongated chord formed of a biocompatible material and being at least partially flexible. The material from which the chord is formed should have sufficient and/or predetermined tensile strength to exert a predetermined tension on the predetermined, prolapsing valve leaflet as the chord extends between a corresponding portion of the heart wall, such as the ventricular wall, as also more fully described hereinafter. The chord is initially housed concentrically within the interior of the introductory sheath, wherein the sheath and the chord are concurrently movable relative to the heart as well as throughout a portion of the interior thereof. As set forth above, the introductory sheath is formed of a material having physical characteristics that allow it to be accurately manipulated so as to be steerable in such a manner that its tip can aim towards the different designated portions of the anterior or posterior mitral valve leaflets that are in the siege of the prolapse.

Also, the exteriorly concentric introductory sheath is movable relative to and along the length of the chord so as to accommodate proper and intended placement and anchoring of the chord within the heart chamber. Therefore, the sheath is movable with the chord into and through predetermined portions of the heart chamber and movable relative to the chord after proper anchoring, securing and/or intended placement of the chord within the heart chamber. Accordingly, the instrument assembly of the present invention also includes an anchor secured to an outer or distal end of the chord. The anchor may also be sufficiently sharpened, pointed or otherwise configured to penetrate an intended heart valve leaflet, such as a prolapsing leaflet of the mitral valve. Further, the penetration and passage of the anchor, the chord, and the introductory sheath substantially through the predetermined valve leaflet may thereby be facilitated.

When properly positioned, the anchor is structured to be secured to a substantially opposing portion of the heart wall, such as the ventricular wall associated with the left ventricle and/or the papillary muscles associated therewith. In order to assure secure anchoring of the distal end of the chord with the corresponding ventricular wall, a gripping structure may be operatively attached to a remainder of the anchor and disposable into an outwardly and/or radially extending orientation. When so disposed, the gripping structure, in combination with the remainder of the anchor, eliminates or significantly restricts the inadvertent detachment of the anchor, and the distal end of the chord attached thereto, from the corresponding ventricular wall portion. In at least one preferred embodiment of the present invention, the anchor and the gripping structure are disposed and applied so as to penetrate the corresponding portion of the ventricular wall but not extend there through. Therefore, the anchored relation of the gripping structure, anchor and the connected distal end of the chord may be defined by a penetration into the interior of the ventricular wall rather than a passage completely there through. Complications associated with sealing and exterior attachment of the chord to the exterior of the ventricular wall are thereby eliminated.

As provided, the present invention further comprises a method of treating heart and valve malfunction utilizing the instrument as generally set forth above. Accordingly, the attendant method comprises, at least in more generic terms, the passing of a portion of the instrument assembly into an intended heart chamber and into penetrating relation to a predetermined valve leaflet, such as a prolapsing leaflet. The sheath, with the chord concentrically disposed on the interior thereof, is passed through the predetermined valve leaflet. Therefore, by virtue of the enclosed disposition of the chord, the chord and sheath will concurrently enter and extend through the predetermined valve leaflet. By manipulation and the application of a positioning force on the sheath, the sheath and the chord will extend across a corresponding heart chamber and into an anchored relation with a substantially opposing portion of the heart wall.

Once the anchor and the connected distal end of the chord are secured to the opposing heart wall portion, the sheath, still concentrically mounted exteriorly of and in enclosing relation to the chord, is withdrawn from heart chamber in which the chord is anchored. More specifically, the sheath is withdrawn by moving relative to and back along the length of the anchored chord in a direction away from the anchor and connected distal end of the chord. The introductory sheath is further withdrawn back through the predetermined valve leaflet while the proximal portion of the chord remains within the valve leaflet. Once the sheath is disposed exteriorly of the valve leaflet and possibly on the exterior of the heart itself, a securing assembly is operatively disposed within the heart chamber in interconnecting relation between a proximal extremity of the chord and the predetermined valve leaflet.

In more specific terms, the securing assembly may include a securing member, which will be mounted on or connected to a proximal portion of the chord and moved along the length thereof into a predetermined, interconnecting position relative to the prolapsing valve leaflet. The position of the securing member will be tailored to and disposed at the exact position needed to achieve correction of the mitral regurgitation, which may be determined by preoperative transoesopageal echography or other preoperative manner, to quantify the occurring mitral regurgitation preoperatively. The securing member then securely interconnects the proximal extremity of the chord to the predetermined valve leaflet and any excess length of the chord will be severed or detached from the proximal extremity of the chord, which is secured to the surface of the leaflet associated with the atrium. The chord is thereby properly tensioned between the opposing, interior corresponding wall portion of the heart and the predetermined valve leaflet so as to overcome the malfunction of the predetermined valve leaflet as explained in more specific details hereinafter.

As emphasized throughout this description, the instrument assembly and attendant method of the present invention is specifically adapted for the treatment of mitral regurgitation. As such, the introductory sheath and the chord, substantially concurrently enter the atrial wall of the left atrium and pass into the interior thereof. Further, the sheath and the chord penetrate and are passed, substantially concurrently, through a prolapsing (flail) anterior or posterior leaflet of the mitral valve into the left ventricle of the heart chamber. Thereafter the sheath and chord are concurrently extended transversely across the left ventricle, wherein the anchor penetrates and is thereby secured in an anchored relation with a substantially opposing portion of the ventricular wall and/or corresponding papillary muscles. The distal end of the chord is connected to the anchor and is thereby secured in an anchored relation to the ventricular wall, by virtue of the penetrating anchor.

Once the distal end of the chord and anchor are in the anchored relation to the ventricular wall, the sheath is withdrawn back along the length of the chord, away from the anchor and the ventricular wall to which the distal portion of the chord is secured. Moreover, the introductory sheath continues to travel back along the length of the chord through the prolapsing anterior or posterior mitral valve leaflet to a location at least exterior to the leaflet, such as within the left atrium and possibly exteriorly of the heart itself.

A securing assembly is then operatively associated with the instrument and is movably disposed along the length of a proximal portion of the chord. In even more specific terms, the movement of the securing assembly and its associated securing member are disposed into an interconnecting position between a proximal extremity of the chord and the mitral valve leaflet penetrated by the chord. As indicated above, proper tensioning is thereby placed on the prolapsing mitral valve leaflet in order to restore a sufficient surface of coaptation between its counterpart, opposing leaflet and maintain the suppressed leaflet in an operative position sufficient to overcome the mitral regurgitation.

Yet another preferred embodiment of the present invention is directed to an instrument assembly and attendant method for treating heart valve malfunction, including mitral valve regurgitation, wherein one of the mitral valves is prolapsing. As further described herein, the treatment procedure of this embodiment involves the positioning of a tensioning cord into the chamber of the heart, preferably through the left atrium. Moreover, the tensioning cord is preferably positioned, using a catheter, sheath and/or other positioning instrument such as, but not limited to, the type set forth above. More specifically, the chord will pass through the mitral valve, preferably through the mitral orifice and between the mitral valve leaflets, into the left ventricle. The distal end of the chord is anchored into the ventricular wall in a position generally opposing the mitral valve being treated. Concurrently, a proximal portion of the synthetic chord remains in a position through the mitral orifice exteriorly of the mitral valve, including at least a part of the proximal portion thereof being disposed in the left atrium.

In order to properly treat a prolapse of affected valve leaflet, the chord is connected to the valve leaflet by securing the proximal portion, more specifically the proximal end thereof to the predetermined mitral valve leaflet. In order to efficiently and effectively accomplish such attachment, this preferred embodiment of the present invention comprises a securing assembly structured to dispose a securing member in interconnecting relation between the proximal end of the chord and the predetermined valve leaflet. Accordingly, the securing assembly comprises a housing including a head portion and a base connected to the housing in a manner which facilitates relative movement of the head portion and the base between an open position and a closed position. Moreover, a capturing area is formed and/or disposed between the head portion and the base when they are in the open position. The disposition, dimension and configuration of the capturing area are such as to facilitate the gripping or other removable but secure engagement of the predetermined leaflet there between. As such, when "gripped" or otherwise removably retained between the head portion and the base as they are moved from the open position towards or into the closed position, the leaflet is disposed and maintained in a "connecting orientation", as described in greater detail hereinafter. It is further emphasized that the term "closed position" is meant to describe the relative positions of the head portion and the base when they are gripping, engaging or otherwise removably but securely retaining the predetermined leaflet there between. Accordingly, it is recognized the closed position may be used to include the head portion and the base not being disposed in direct confronting or engaging relation to one another.

Additional details of the securing assembly include a positioning member, which may be in the form of a plunger or like structure, capable of being disposed in driving engagement with the head portion. As a result, manipulation of the housing to the extent of moving the positioning member it into a driving engagement with the head portion forces the head portion towards the base and into or towards the closed position and/or in gripping and removably retaining relation to the predetermined valve leaflet disposed within the capturing area. In order to facilitate return orientation of the head portion and base into the open position, when it is intended to release of the predetermined leaflet, a biasing structure is disposed to normally bias head portion into or towards the open position.

The securing assembly also includes a retaining assembly disposed on both the head portion and the base. As such, the retaining assembly is structured to removeably retain the securing member in a position which facilitates the connection of the securing member to the predetermined valve leaflet, before relative movement of the head portion and base and subsequently, as the head portion and base are relatively disposed from the open position and into or towards the closed position.

In more specific terms, the retaining assembly comprises first and second retaining segments each disposed on a different one of the head portion and base. Further, the first and second retaining segments are disposed and structured to removeably retain the first and second segments of the securing member, at least initially in spaced relation to one another, when the head portion and the base are in the open position. As also discussed in greater detail hereinafter, at least one embodiment comprises the first and second securing segments being respectively defined by a penetrating segment and a receiving segment. Therefore, when the penetrating and receiving segments are appropriately disposed in the first and second retaining segments, when in the open position, a proximal portion of the chord is connected to the base, as well as to the second retaining segment associated with the base. Accordingly, an "interconnecting relation" of the securing member relative to the predetermined leaflet comprises the penetrating segment disposed in penetrating relation through the valve leaflet, retained within the capturing area, when the head portion and base are disposed into the closed position.

Moreover, the accompanying method for treating mitral valve regurgitation using the instrument assembly, as generally set forth above, includes connecting the proximal portions of the chord to the securing member and the securing assembly, once the distal end of the chord is anchored in the ventricular wall. As indicated, when the distal end of the chord is anchored to the ventricular wall, the proximal portion of the chord will extend through the mitral orifice, between the valve leaflets, rather than penetrating through a valve leaflet, as with at least some of the preferred embodiments of the present invention, as described above. As such, the proximal portion of the chord is then connected to the valve leaflet by the securing member. Moreover, the proximal portion of the chord is connected to the securing assembly and the penetrating segment and the receiving segment are removably disposed within the corresponding first and second retaining segments, while the head portion and base are in the open position.

Accordingly, the chord will be properly tensioned and connected to the valve leaflet when its distal end is anchored to the ventricular wall and a proximal end of the proximal portion is connected to the predetermined valve leaflet. Such connection comprises the penetration of the penetrating segment through the predetermined valve leaflet and the receiving segment concurrently to the proximal end of the chord be being connected to the receiving segment and the base.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 10A is a sectional view in partial cutaway of a portion of the embodiment of FIG. 10.

Like reference numerals refer to like parts throughout the several views of the drawings.

DETAILED DESCRIPTION OF THE PREFERRED EMBODIMENT

Figure 1:
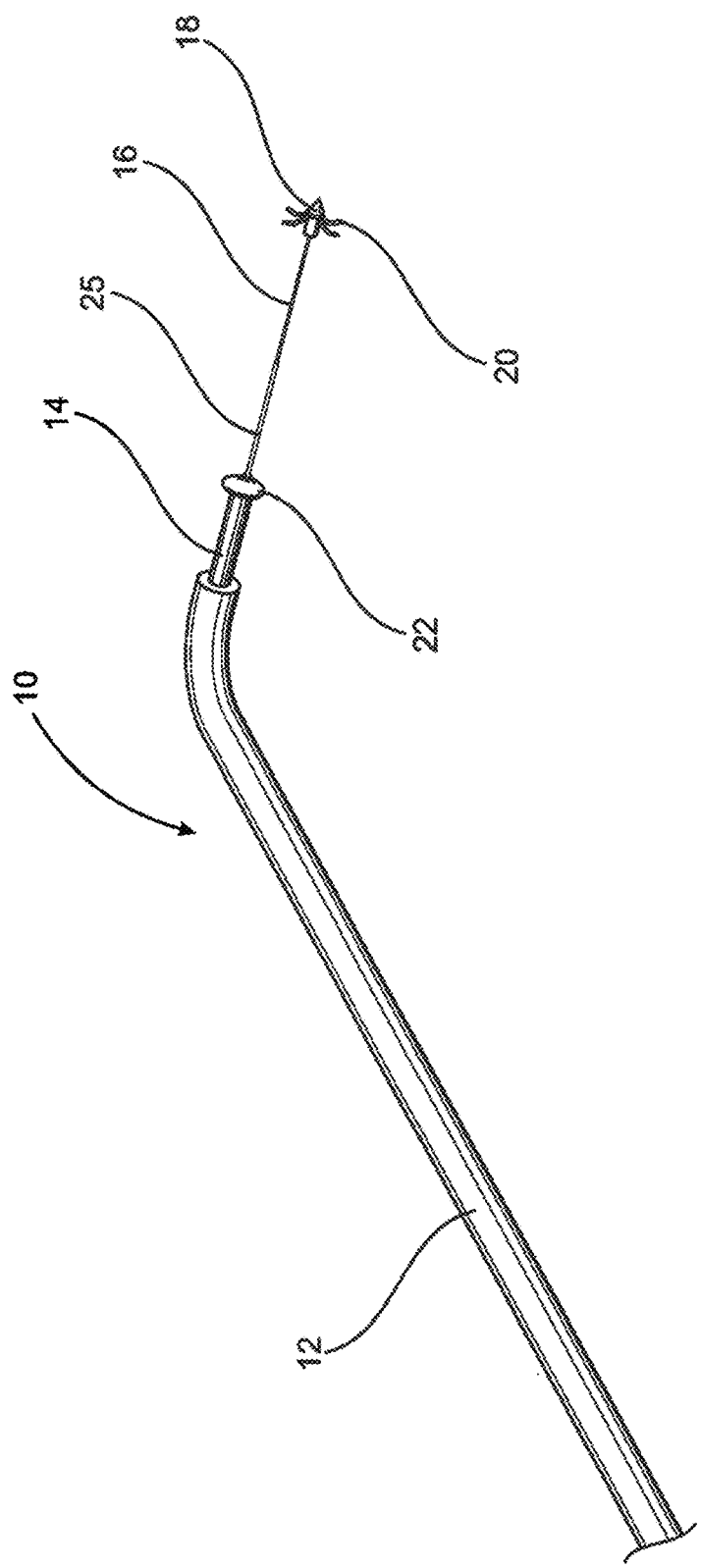
FIG. 1 is a perspective view of one preferred embodiment of the instrument assembly of the present invention used in the treatment of heart valve malfunction.
Figure 1A:
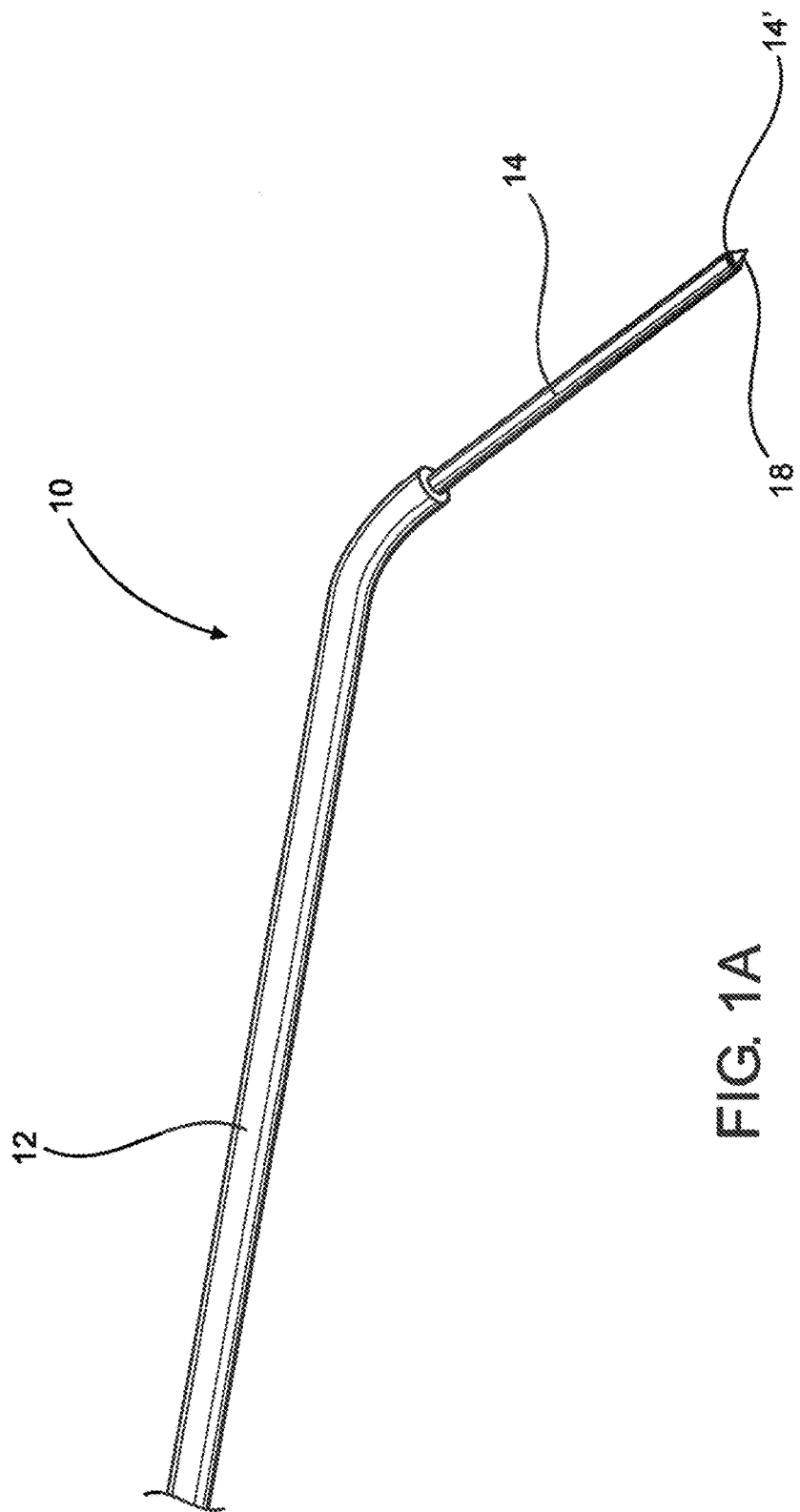
FIG. 1A is a perspective view of the instrument assembly of the embodiment of FIG. 1 in an initially introductory position.

As represented in the accompanying drawings and with specific reference to FIGS. 1 and 1A, the instrument assembly of the present invention is schematically and generally indicated as 10 and is used for the treatment of heart valve malfunction generally and more specifically for the treatment of mitral regurgitation. As such, the instrument assembly 10 includes an elongated delivery catheter or tube 12 having a hollow interior and structured to deliver operative portions of the instrument assembly 10 to the treatment site within the heart of a patient. As such, the elongated delivery catheter or tube 12 is dimensioned and configured to enter the chest cavity through appropriate introduction instrumentation. The delivery tube 12 is formed of a material and/or includes positioning structure or linkage incorporated therein which facilitates the maneuvering or steering thereof to a point at least generally exterior the heart and more specifically the atrial wall of the left atrium. However, the at least semi-rigid material of the delivery tube 12 should be sufficient to also facilitate proper manipulation so as to position or "steer" the remainder of the instrument assembly 10 to the intended location within the interior thereof, as well as facilitate penetration of and anchoring to intended tissue portions.

The instrument assembly 10 also includes an introductory sheath 14 movable within the delivery tube 12 and an elongated flexible material chord 16. The introductory sheath 14 is concentrically and movably enclosed within the delivery tube 12 and the sheath 14 is movably disposed concentrically about the chord 16. It is emphasized that FIG. 1 represents a completely assembled instrument assembly 10. However, as will be described in detail with the schematic representations of FIGS. 1 through 9, the various portions of the instrument assembly 10 are used in successive steps to accomplish installation relative to the affected portions of the heart valve being treated.

Accordingly, the instrument assembly 10 further includes the elongated flexible material chord 16 which may be formed of a synthetic, biocompatible material. An anchor 18 is fixedly secured to the outer or distal end of the chord 16 and is movable therewith relative to the introductory sheath 14. As clearly represented in FIG. 1A chord 16 is at least initially enclosed concentrically within the interior of the introductory sheath 14, wherein the sheath 14 is movable along the length of the chord 16. Further, the sheath includes an open distal end 14' serving to at least partially encloses or be registered alignment with the anchor 18. Therefore, FIG. 1A represents cooperative portions of the instrument assembly 10 at least upon initial entry of the introductory sheath 14 and anchor 18 into the interior of the heart 30, as specifically described in detail in FIGS. 2 through 9, hereinafter described.

Therefore, with further regard to FIG. 1A, the positioning of the anchor 18, the introductory sheath 14 and the chord 16 is such that the chord 16 is disposed within the interior of the introductory sheath 14. Further, the anchor 18 is disposed at least partially within and/or in an exposed relation to the open distal end 14' of the sheath 14. In addition, the anchor 18 has a sharpened, pointed or other appropriate configuration for penetrating portions of the heart. The anchor 18 may also include a gripping structure 20 which may be initially disposed in a collapsed position when the anchor 18 is in registry with the distal opening 14' of the sheath 14. However, upon removal or exposure of the anchor 18 and a length of the chord 16 from an interior of the sheath 14, the gripping structure 20 may include an inherent bias causing it to expand outwardly and/or radially from the remainder of the anchor 18. This gripping structure 20 is provided to facilitate a secure engagement of the anchor 18 with predetermined heart wall portions, when the instrument assembly 10 is properly applied in the treatment of the heart valve malfunction.

With further reference to FIG. 1 the assembled representation of the instrument assembly 10 further includes the provision of a securing member 22 which may travel along the length of the chord 16. The securing member may be forcibly positioned into an intended interconnecting location relative to a heart valve leaflet in order to accomplish a secure attachment of the chord 16 to the leaflet as will be explained in greater detail hereinafter. Such an interconnecting placement of the securing member 22 relative to both the chord 16 and the affected valve leaflet serves to establish and maintain a sufficient tension and/or positioning force on the predetermined valve leaflet to suppress movement thereof, as explained hereinafter with regard to FIGS. 2 through 9.

As schematically represented in FIGS. 2 through 9, the heart is generally indicated as 30 and includes the representative portions including the left atrium 32, the left ventricle 34 and the mitral valve 36, including the anterior and posterior mitral valve leaflets 38 and 38', respectively. As additionally represented, the left ventricle 34 is at least partially bordered or surrounded by ventricular wall 40 which may be directly associated with corresponding papillary muscles (not shown) facilitating the proper positioning of the mitral valve leaflets 38 and 38' through organic tissue tethering, as generally outlined above.

For purposes of clarity, FIGS. 2-9 schematically represent the instrument assembly 10 used on the anterior leaflet 38 of the mitral valve 30 in order to treat and correct mitral regurgitation. However, it is emphasized the instrument assembly 10 and the attendant method of the present invention may be applied to an anterior and/or the posterior prolapsing leaflet in the manner described herein, in correcting a mitral regurgitation condition of the heart. Moreover, while the various embodiments of the present invention are described using a single chord 16, a plurality of chords 16 may be used with the cooperative instrument components of the instrument assembly 10.

Figure 3:
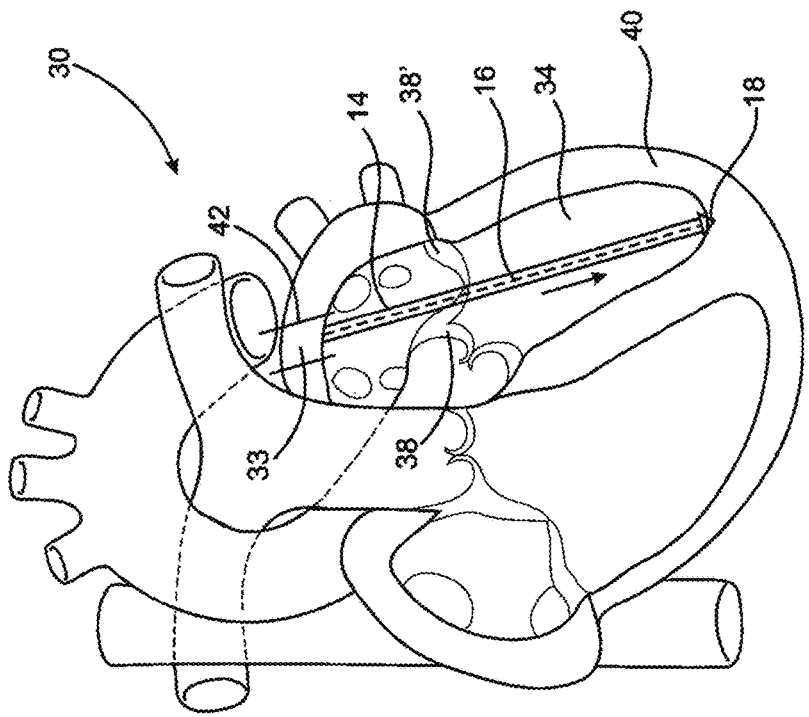
FIGS. 2 through 9 are schematic representations of successive steps in the attendant method of utilizing and applying the instrument assembly of the embodiment of FIGS. 1 and 1A specifically for the treatment and correction of mitral regurgitation.
Figure 2:
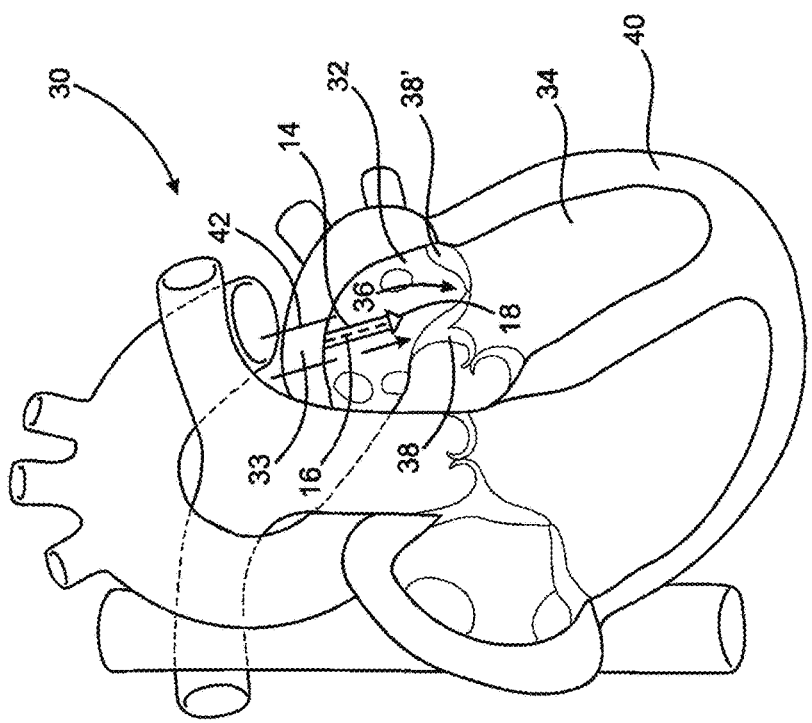

With initial reference to FIGS. 2 and 3, the instrument assembly 10 is introduced into the interior of the heart 30 and more specifically into the left atrium 32, through the atrium wall 33, using an appropriate introduction assembly 42. Therefore, the introductory sheath 14 and the chord 16 located concentrically within the sheath 14 will concurrently pass through the atrial wall 33 of the heart into the left atrium 32, as it is directed towards the anterior leaflet 38 of the mitral valve 36. It should be further noted that the anchor 18 is at least initially in the position generally represented in FIG. 1A. Due to its predetermined configuration the anchor 18 will serve to approach and penetrate the anterior leaflet 38 of the mitral valve 36 as clearly represented in FIG. 3.

In addition, the penetration of the anterior leaflet 38 initially by the anchor 18 will facilitate the penetration and passage, substantially concurrently, of the chord 16 and the introductory sheath 14 through the anterior leaflet 38 as schematically represented. As further represented in FIG. 3, a continued force will be applied to the introductory sheath 14 causing the sheath 14 and interiorly disposed chord 16, as well as the anchor 18 to continue concurrent passage through the anterior valve leaflet 38 until the anchor 18 reaches, penetrates and is secured to the ventricular wall 40 and/or correspondingly disposed papillary muscles associated therewith.

Figure 4:
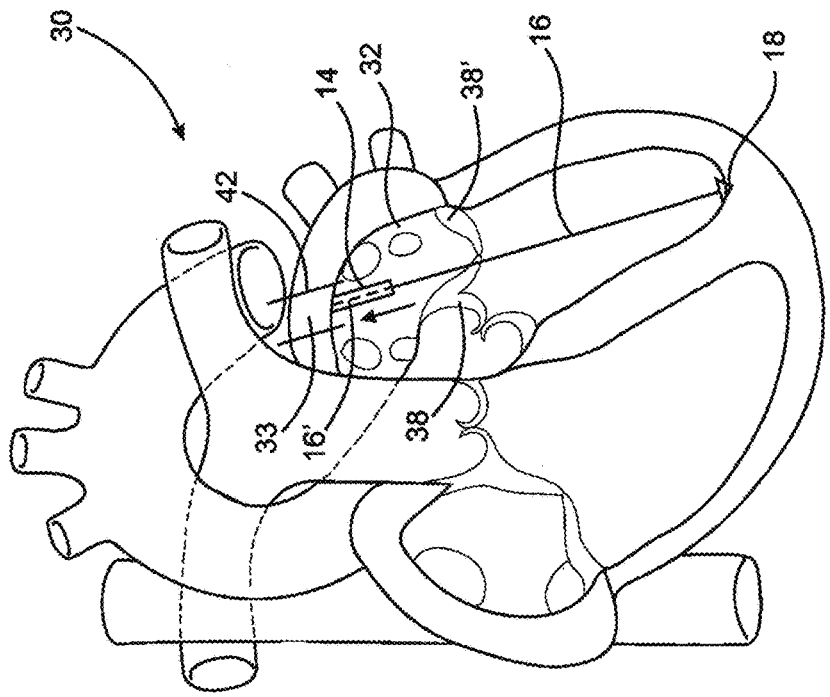
Figure 5:
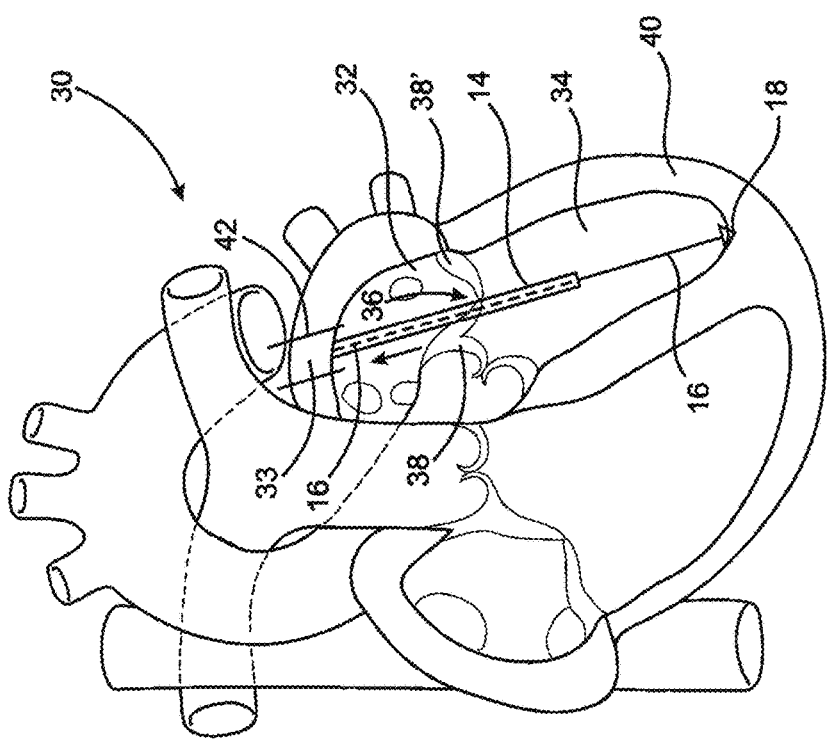
Figure 7:
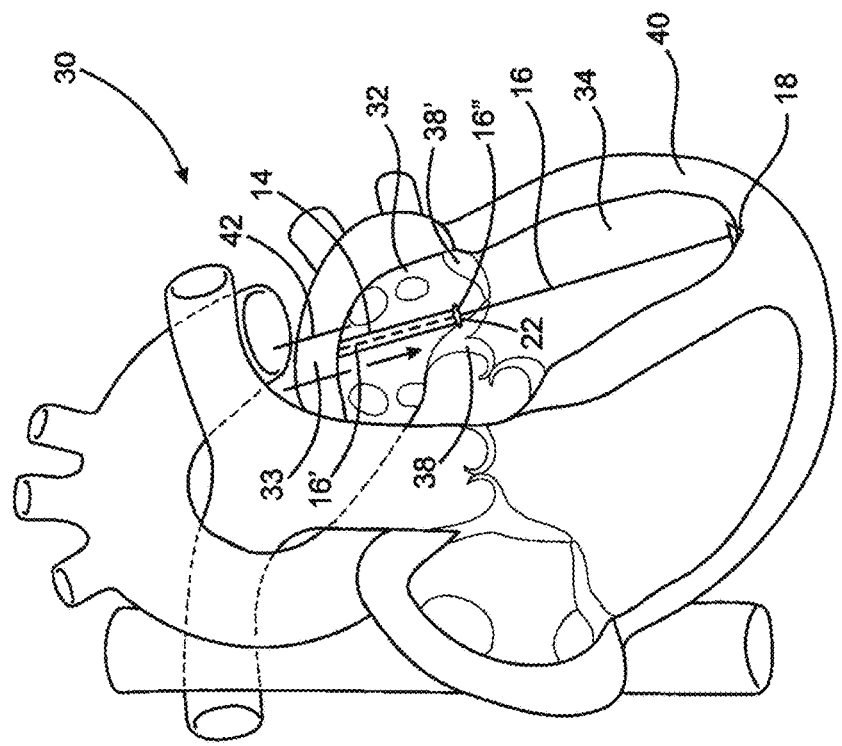
Figure 6:
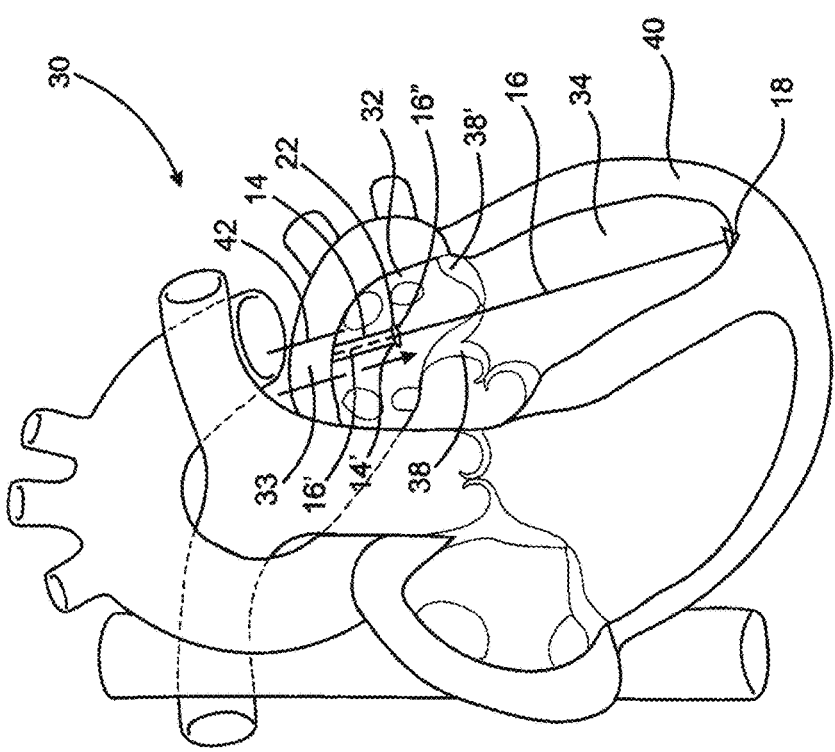
Figure 8:
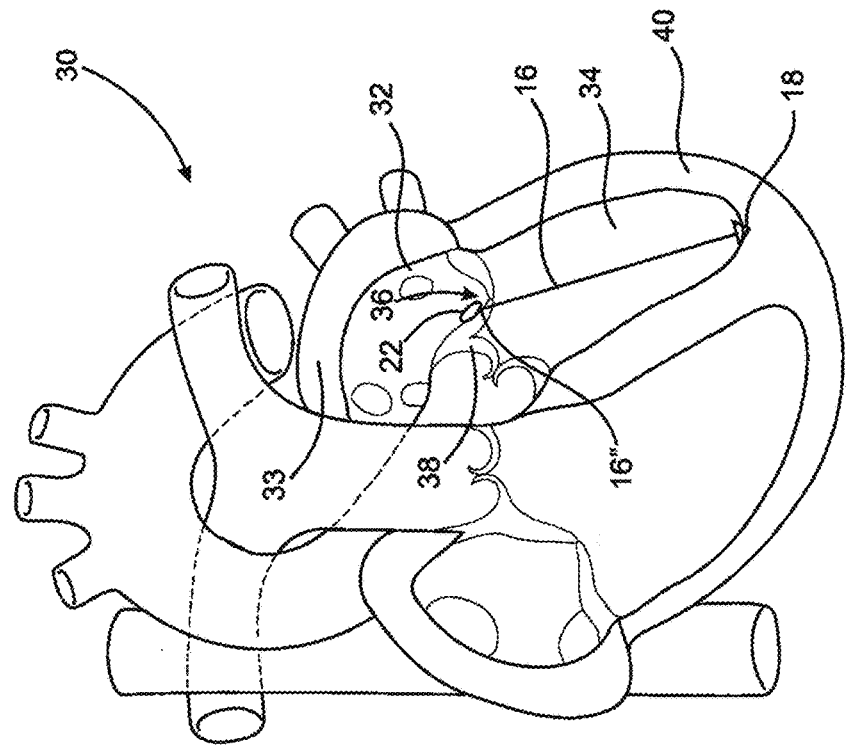

As best represented in FIGS. 4 and 5, once the anchor 18 is secured to the ventricular wall 40 and/or the corresponding papillary muscles, the distal end of the chord 16 will be affixed to the ventricular wall 40 and remain in place as the introductory sheath 14 is withdrawn back along the length of the chord 16, as indicated by the directional arrows. As the introductory sheath 14 is withdrawn back along the length of the chord 16, the aforementioned gripping structure 20 will have been expanded into a gripping orientation. When the gripping structure 20 is so oriented, the anchor 18 and the distal end of the chord 16 connected thereto will be reliably anchored or connected to the ventricular wall 40. Continued withdrawal of the introductory sheath 14 will result in its passage back through the initially penetrated and suppressed mitral valve leaflet 38, as clearly represented in FIG. 5. As such, the majority of the length of the chord 16 will thereby be exposed and maintained in the represented position within the left ventricle and between the ventricular wall 40 and the penetrated (suppressed) leaflet 38, while the introductory sheath 14 passes back through the introduction assembly 42 and out of the interior of the left atrium 32, through the atrium wall 33. Therefore, the proximal portion 16' of the chord 16 remains in place, within the left atrium 32, and may serve effectively as a guide or otherwise facilitate the placement of the securing member 22, as represented in FIGS. 6 through 9.

More specifically, once the introductory sheath 14 is removed from the left atrium 32, through the introduction assembly 42, the securing assembly, including securing member 22, will move along the length of the chord 16 as it is introduced into the left atrium 32 such as through the atrium wall via, the introduction assembly 42. As schematically represented, the securing member 22 will be forced, moved, positioned, etc. along the proximal portion or length 16' of the chord 16 by any appropriate technique and/or appropriate positioning instrument/device, which may be incorporated or operatively associated with the chord 16. Positioning of the securing member 22 will continue until it is disposed in engaging, interconnecting and at least partially protective or sealing engagement with an exterior surface portion of the suppressed anterior mitral valve leaflet 38 located within the left atrium 32. The position of the securing member 22 will be disposed in the exact position, on and along the length of the chord 16 needed to position and or suppress movement of the leaflet 38 to achieve correction of the mitral regurgitation. Such exact positioning may be determined by preoperative transoesopageal echography or other preoperative manner to quantify online mitral regurgitation preoperatively.

With further regard to the positioning of the securing member 22 into the interconnecting relation between the proximal extremity of chord 16 and the anterior leaflet 38. One embodiment may also include a guiding element or sleeve 25, as represented in FIG. 1. When utilized, the element 25 will be disposed at a predetermined position along the length on the artificial chord 16 and be mounted concentrically about and/or along a portion of the chord 16. As applied, the guiding element 25 may assume and or be at least partially defined by a variety of different structures, devices and/or mechanisms other than, but possibly including, the schematically represented sleeve. Accordingly, the guiding element is operative to accurately center or otherwise dispose the securing member 22 in sealing and/or covering relation to the aperture or area where the chord 16 remains in its extended position through the anterior leaflet 38. Further, the securing member 22 securely connects the proximal extremity 16" of the chord 16 to the valve leaflet 38 and any excess length of the proximal portion 16' of the chord 16 will be severed or detached from the extremity 16" of the chord 16 and the securing member 22, which interconnects the proximal extremity 16" to the "exterior" surface of the leaflet 38 exposed to the left atrium 32.

With continued reference to FIGS. 5 through 8, manipulation of the instrument of the assembly 10, such as by medical personnel manipulating the delivery catheter 12 causes a severing of the proximal extremity from a remainder of the chord 16. As a result, the securing member 22 serves to securely connect and fasten the chord 16 to the exterior of the anterior leaflet 38, disposed within the left atrium 32. Upon a secure connection of the securing member 22 to the exterior side or surface of the anterior leaflet 38, the introductory sheath 14 passes back through the introduction assembly 42 so as to exit the left atrium 32 and the remainder of the heart. Thereafter, the introduction assembly 42 is also removed from its initial operative position.

Figure 9:
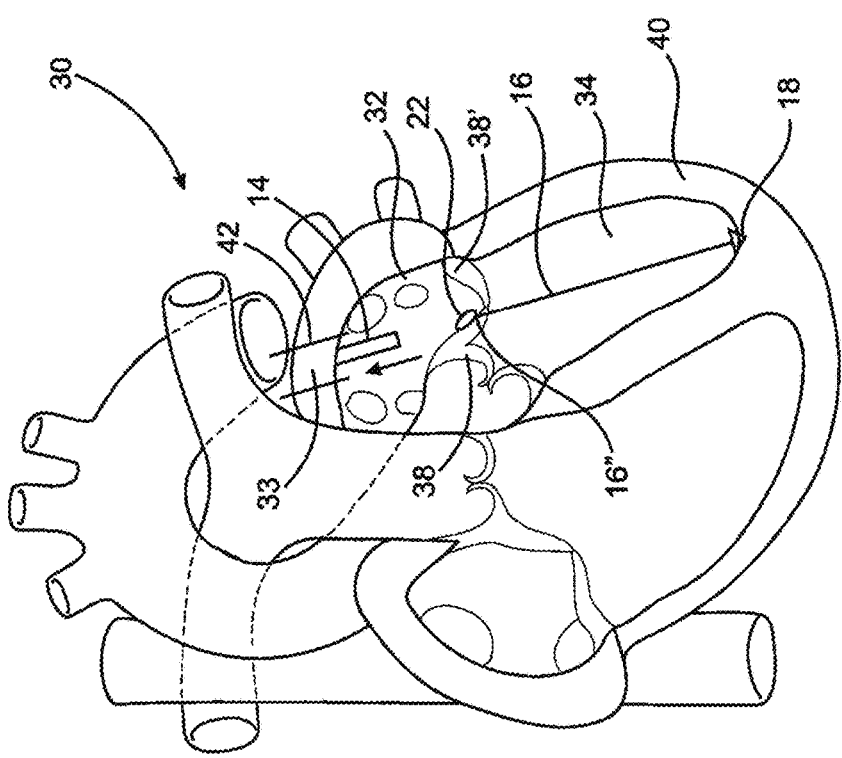

Therefore, as represented in FIG. 9 the heart 30 is represented with the synthetic chord 16 properly anchored between the ventricular wall 40 and the penetrated anterior leaflet 38. In this position, proper tensioning or positioning forces are applied to the anterior leaflet 38 causing it to be positioned in a manner which effectively overcomes mitral regurgitation, as set forth above.

As schematically represented in FIGS. 10 through 16, the present invention comprises yet another preferred embodiment directed to a securing assembly generally indicated as 50. The securing assembly 50 and its method of use is directed to the attachment of the proximal portion or proximal end of a cord 116, subsequent to it being anchored, as at 18 in the ventricular wall 40 of the heart 30. Similar to the embodiments represented in FIGS. 2 through 5, as set forth above, the synthetic cord 116 is operatively positioned within the left ventricle 34 by means of a sheath 14 or alternatively structured "spear" or like instrument introduced into the left atrium 32 through a heart wall, 33 utilizing an introduction assembly 42. The introduction assembly 42 may be, but is not limited to, the type of introduction assembly represented in the currently pending U.S. patent application Ser. No. 13/691,087 to the inventor herein. One distinguishing feature of the present invention includes the introduction of the cord 116 into the left ventricle 34 through the mitral orifice and/or between the interior and posterior mitral valve leaflets 38 and 38' respectively. This differs from the embodiments 2 through 5 wherein the sheath 14 and/or substantially equivalent spear or like structure penetrates one of the leaflets 38, 38' under treatment, such that a proximal portion of the cord 16 extends through the predetermined leaflet under treatment.

Figure 10:
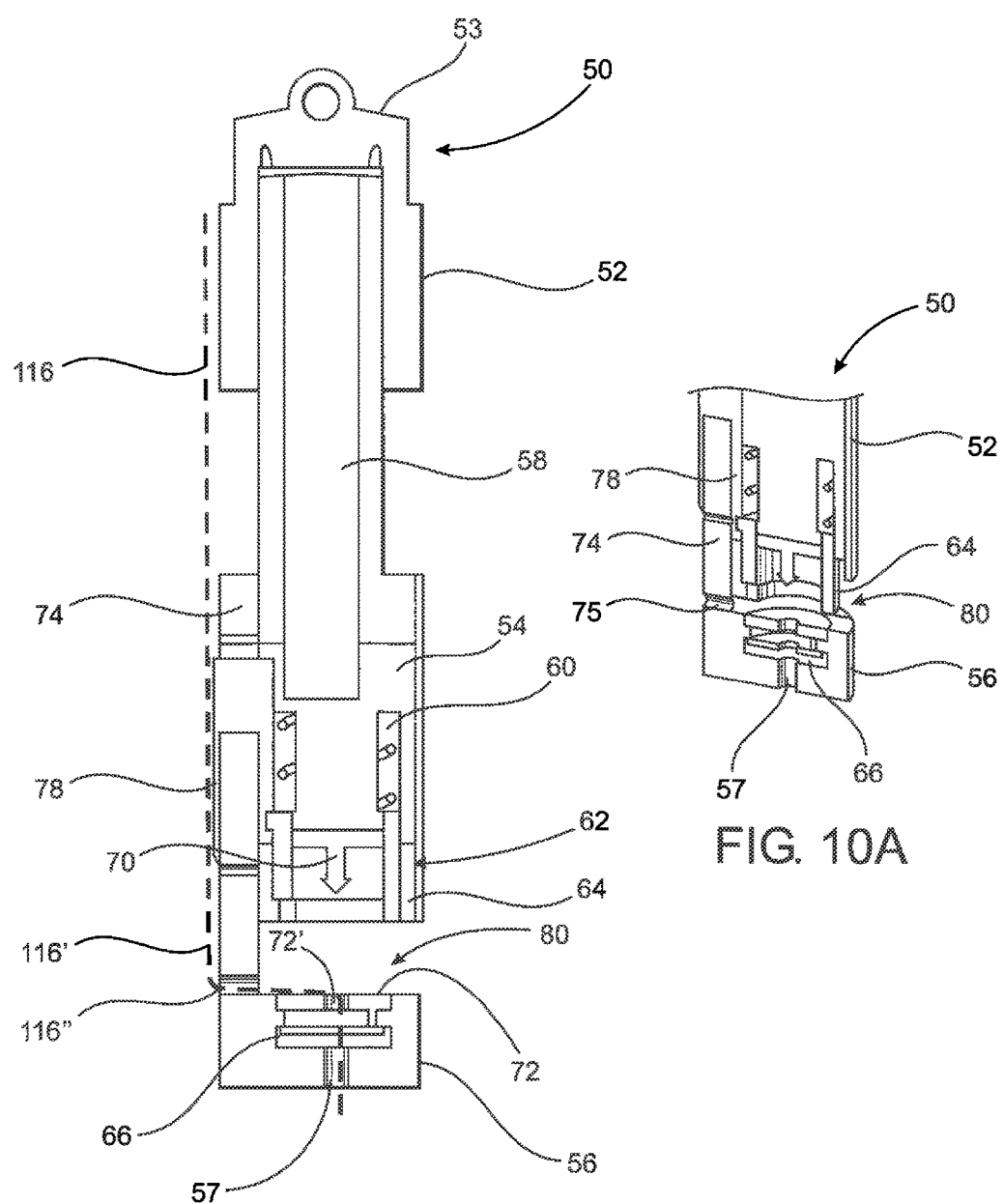
FIG. 10 is a schematic representation of yet another preferred embodiment of the present invention directed to a securing assembly for connecting a proximal end of a tensioned chord to a valve leaflet.
Figure 11:
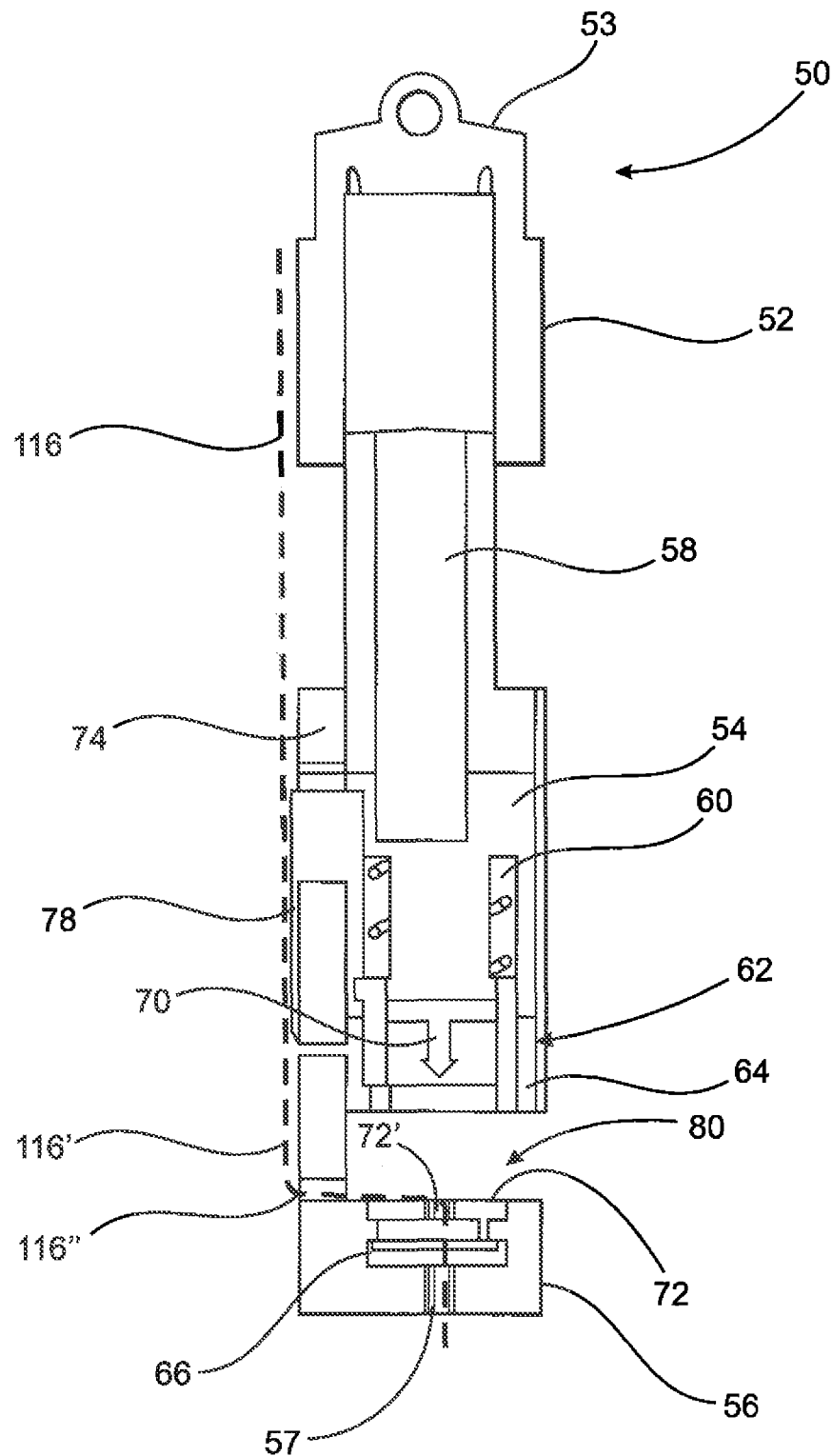
FIG. 11 is a schematic representation of the embodiment of FIG. 10 in a successive, operative position.
Figure 12:
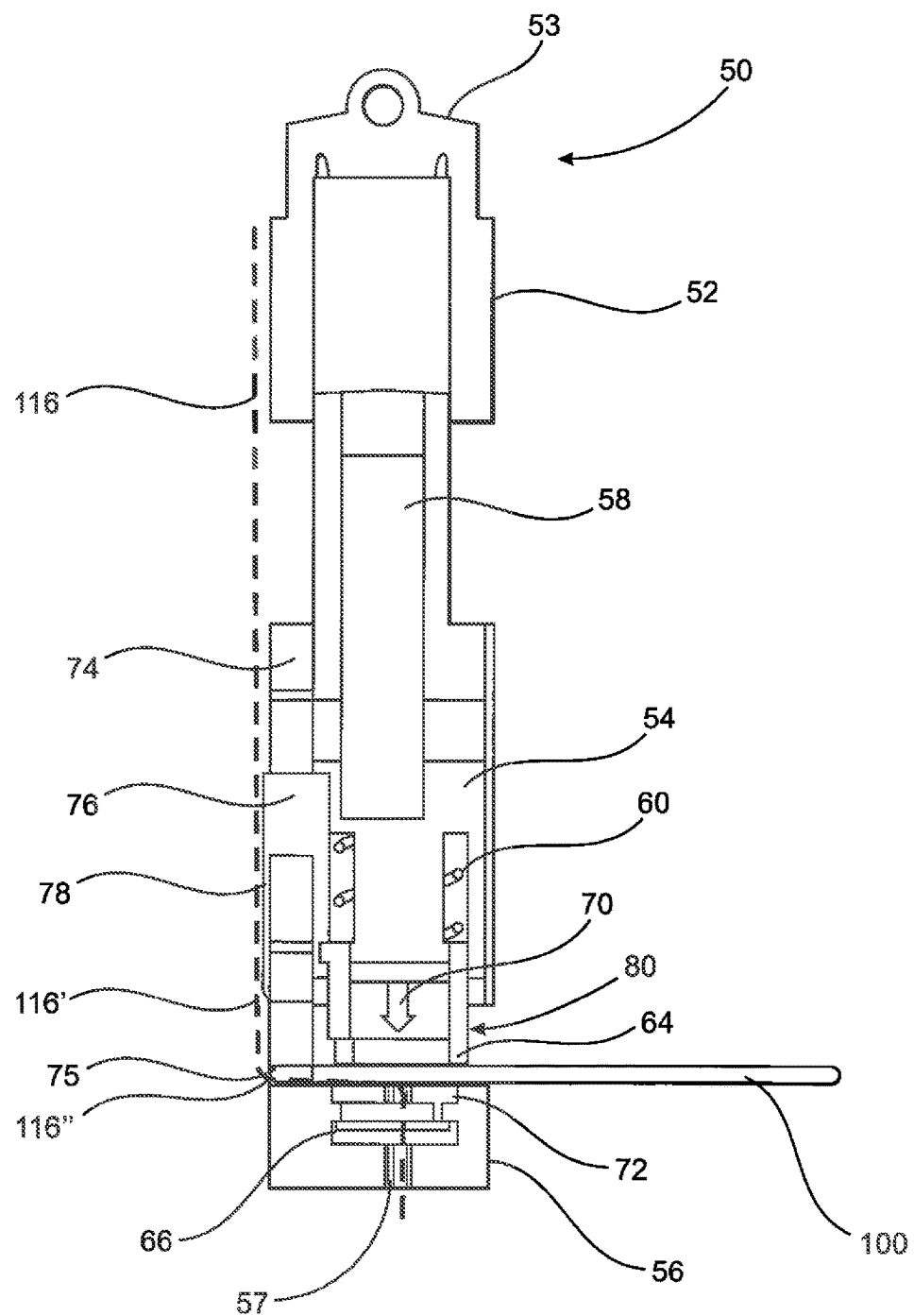
FIG. 12 is a schematic representation of the embodiment of FIGS. 10 through 11 in a successive operative position.
Figure 13:
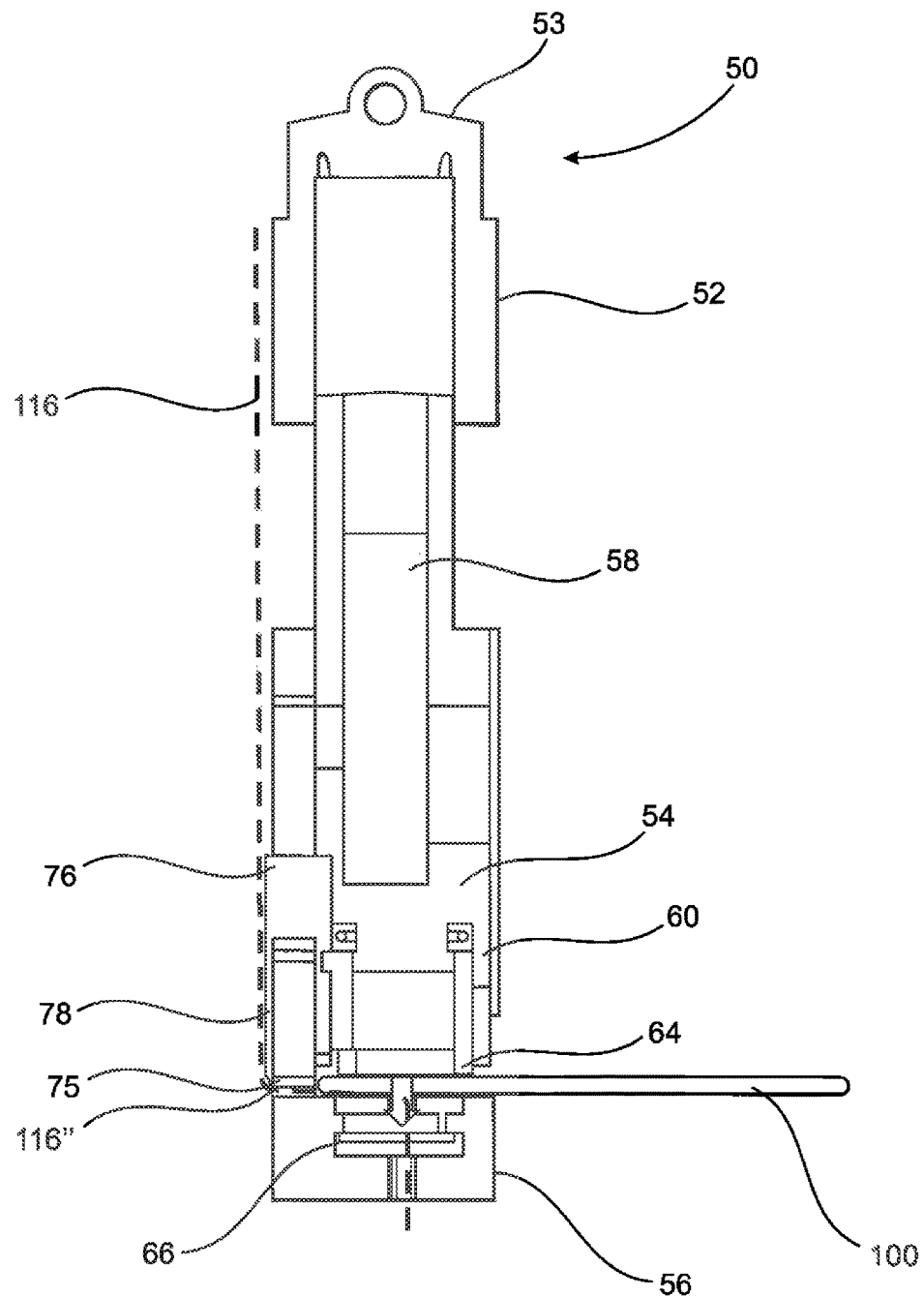
FIG. 13 is a schematic representation of the embodiment of FIGS. 10 through 12 in a successive operative position.
Figure 14:
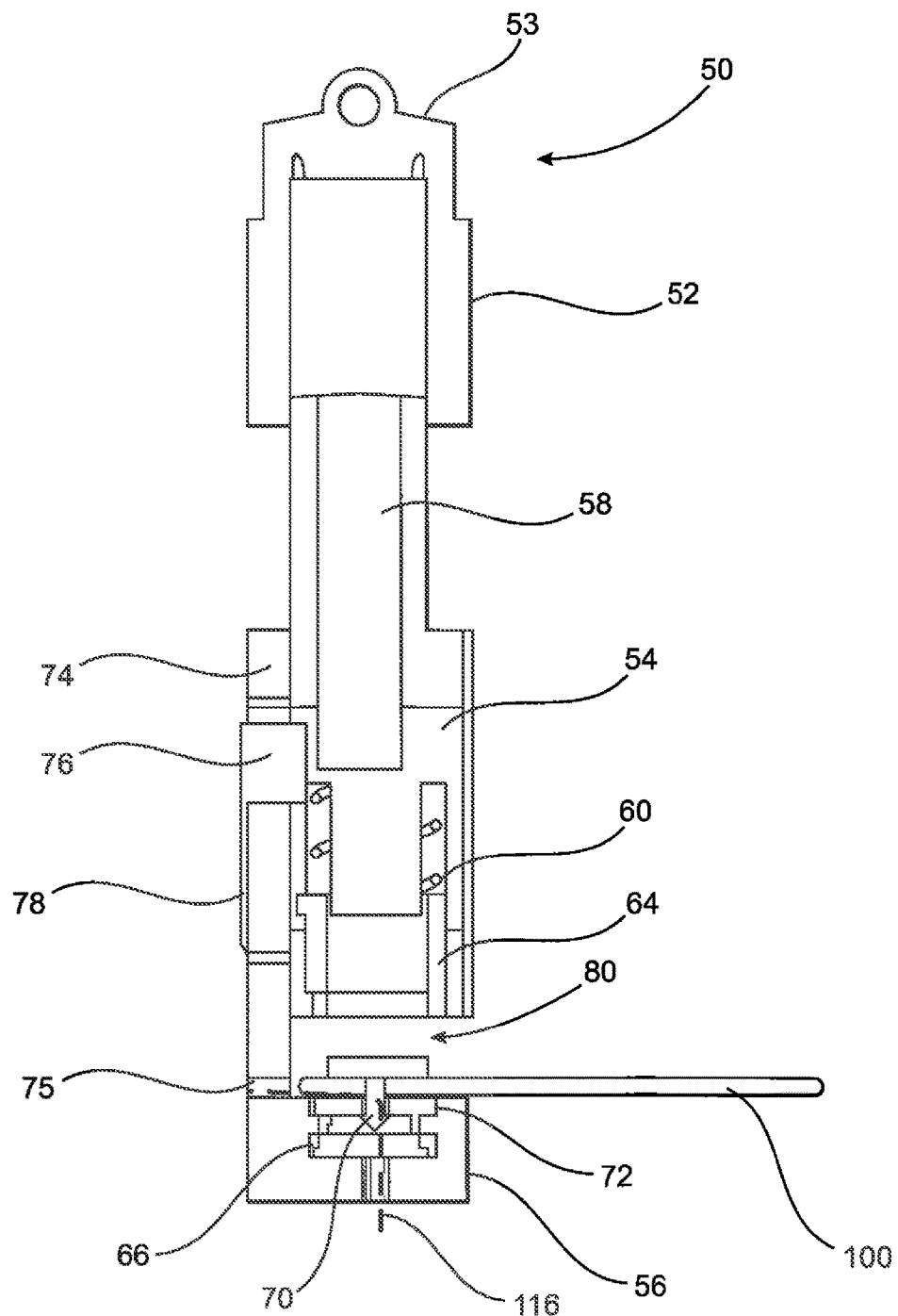
FIG. 14 is a schematic representation of the embodiment of FIGS. 10 through 13 in a successive operative position.
Figure 15:
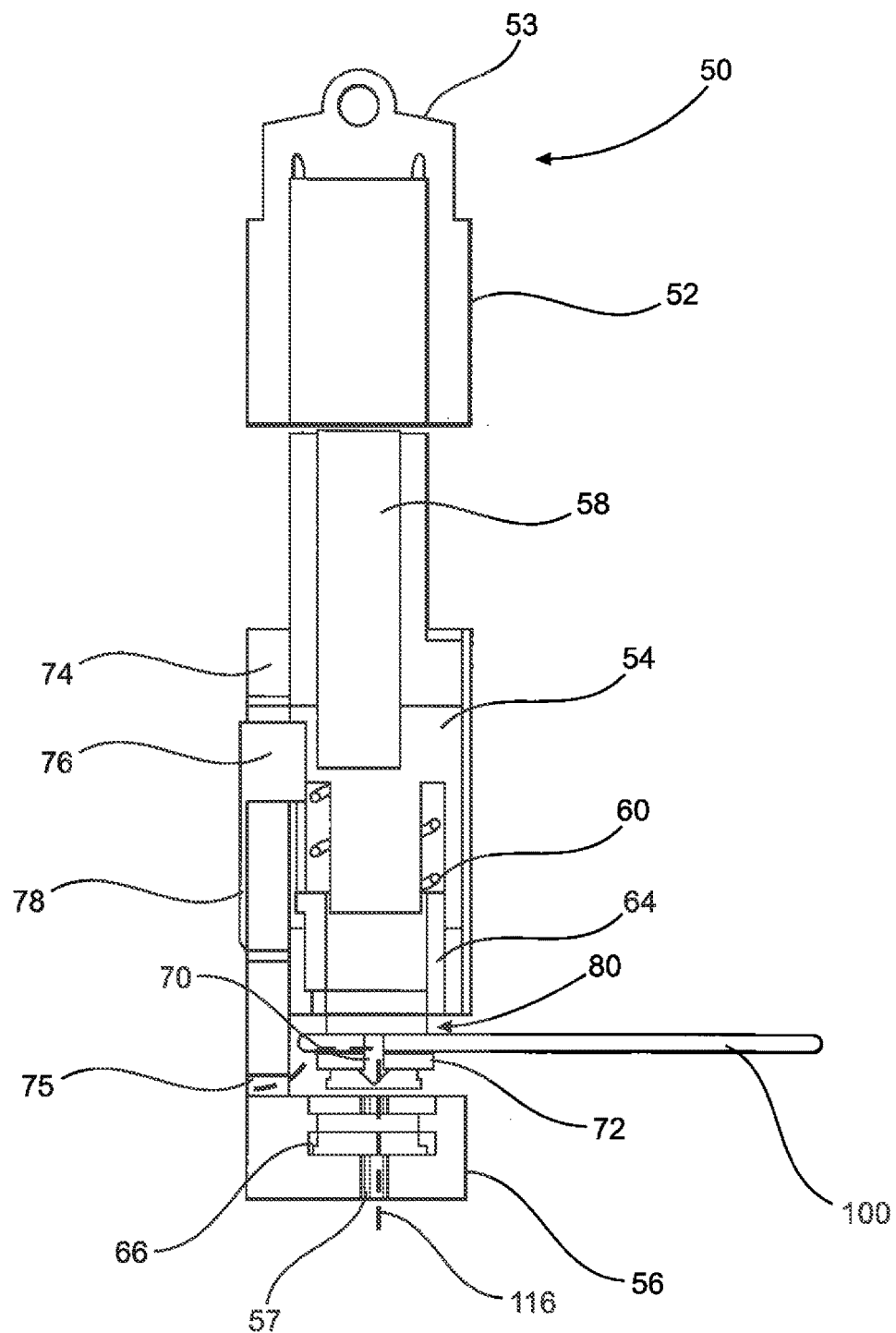
FIG. 15 is a schematic representation of the embodiment of FIGS. 10 through 14 in a successive operative position.

Moreover, the securing assembly 50 of this additional preferred embodiment of the present invention is intended to secure a securing member in attached, interconnecting relation between a proximal portion 116' or a proximal end 116" of the cord 116 to the predetermined valve leaflet being treated. Accordingly, the securing assembly 50 includes a housing generally indicated as 52 having a head portion 54 and a base 56 moveably disposed relative to one another between an open position, as represented in FIGS. 10 and 11 and a substantially closed position, as successively represented in FIGS. 12 and 13. In accomplishing the disposition of the head portion 54 and base 56 between the open and closed positions, a positioning member and/or plunger 58 is mounted on and/or within the housing 52. As such the positioning member 58 is capable of being manipulated so as to force the head portion 54 from the open position, as represented in FIGS. 10 and 11, into the closed position, as generally represented in FIGS. 12 and 13. Therefore, the positioning member 58 may be in the form of a plunger type structure, which may be activated, controlled and/or operated by appropriate manipulation of the end 53 or other appropriate portion of the housing 52.

It is of further note that the housing 50, including all of the operative and structural components associated therewith, is sufficiently dimensioned to pass through an appropriately disposed and dimensioned introduction assembly 42 of the type at least generally described above.

Other structural and operative features of the securing assembly 50 includes a biasing structure 60 mounted on the housing 52 in substantially biasing relation to at least the head portion 54 and at least a portion of a retaining assembly generally indicated as 62. As will be explained in greater detail hereinafter with regard to the method of use or operation of the securing assembly 50, the retaining assembly 62 includes a first retaining segment 64 connected to and moveable with the head portion 54, as well as a second retaining segment 66 connected to or mounted to the base 56. As such, retaining assembly 62 is disposed on or connected to both the head portion 54 and base 56 is structured to initially and removeably retain a securing member 68 thereon. Moreover, the securing member 68, as used in combination with the securing assembly 50, includes a multi-part structure, comprising a first or penetrating securing segment 70 and a second or receiving securing segment 72. Each of the first and second securing segments 70 and 72 is structured to assume an interconnecting relation between the cord 116 and more specifically a proximal end 116" thereof and a predetermined valve leaflet 100 involved in the procedure.

Yet additional features of the securing assembly 50 includes a connecting linkage 74 mounted on the housing 52 and serving to moveably support at least the head portion 54 and structured for the movement of the positioning member or plunger 58. As such, the head portion 54 and/or plunger 58 are collectively disposed from the open position into the closed position.

In addition a severing or disconnecting member 76 is also mounted on the housing in interconnected relation to the head portion 54. The severing member is moveable with the head portion 54 when it is disposed between the open and closed positions. As described with specific reference to FIGS. 13 and 14, the disconnecting or severing structure 76 may include a severing blade or like member 78 connected to the severing structure 76 and moveable therewith and with the head portion 54 as it is forced by the positioning member or plunger 58 from the open position of FIGS. 10 and 11 into the closed position of FIGS. 12 and 13. As indicated, the blade 78 will serve to cut or otherwise disconnect a remainder of the proximal portion 116' of the cord 116 from what may be accurately referenced to as a proximal end 116" of the cord 116.

The primary reference to FIG. 10 A and as further represented throughout the remaining FIGS. 10 through 16, the base 56 as well as connecting linkage 74 includes an at least partially slotted or apertured construction, such as at 57 and 75 respectively. Accordingly, prior to disposition of the first and second securing segments 70 and 72 in an interconnecting relation to both the cords 116 and leaflet 100, a proximal portion 116' of the cord 116, including the proximal end 116", is connected to the base 56, receiving segment 72 and the connecting linkage 74. Such connection may occur by an at least partial "threading" thereof through the respective slots or openings 57, 72', and 75 respectively. As clearly represented in FIG. 10A, the structure of the base 56, receiving securing segment 72 and the connecting linkage 74 may have an at least partially open, apertured or otherwise appropriately configured structure which facilitates the "threading" or other type of connection of the proximal portion 116' of the cord 116 and/or proximal end 116" to and/or through the base 56, the receiving securing segments 72 and the linkage 74.

Figure 16:
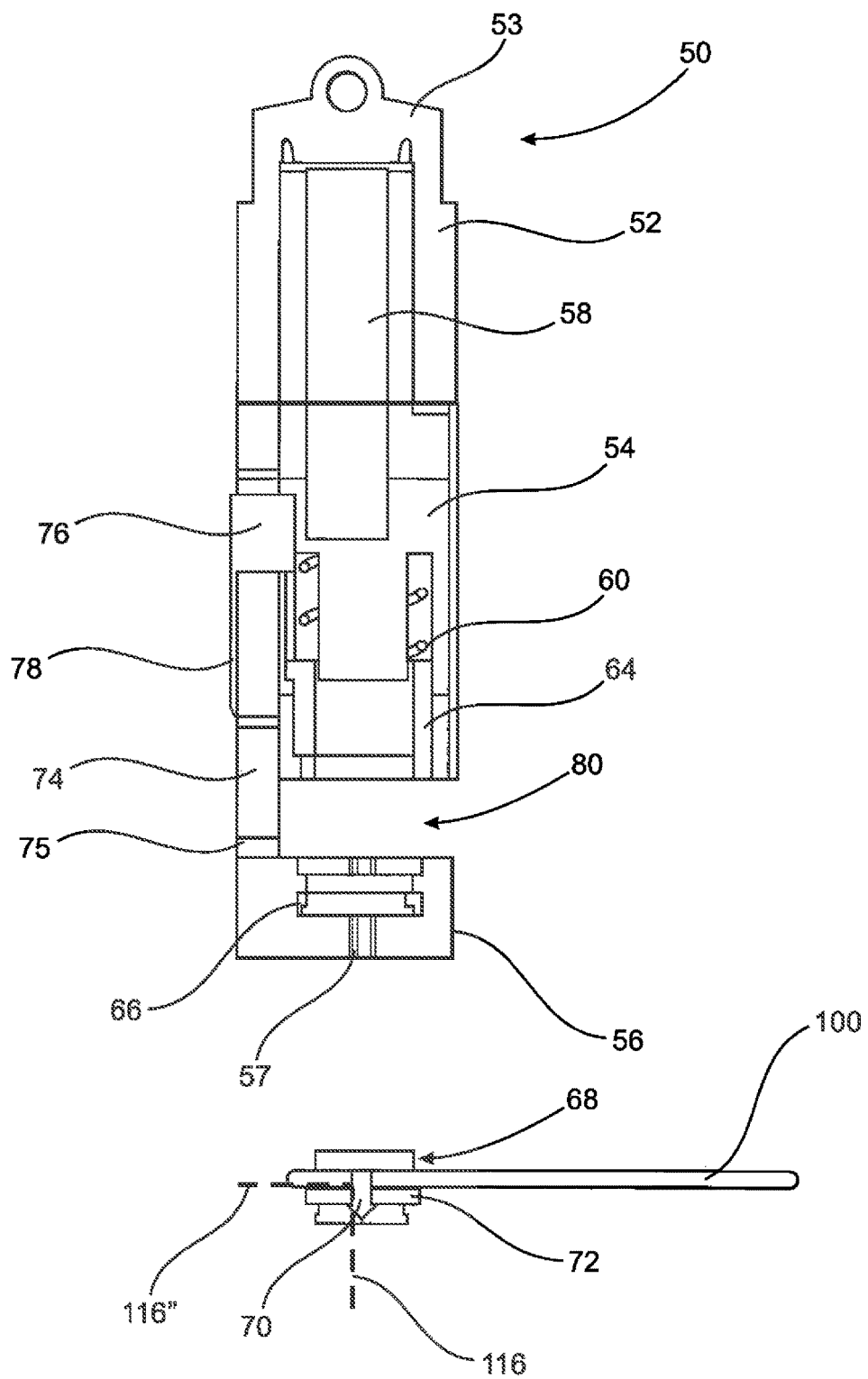
FIG. 16 is a schematic representation of the embodiment of FIGS. 10 through 15 in a successive operative position.

As represented throughout FIGS. 1 through 16 and with reference to FIGS. 2 through 5 as well as 11 through 16, a method of use and/or application of the securing assembly 60 may be directed to a method of treating a heart valve malfunction specifically including, but not limited to, the treatment of mitral valve regurgitation. As such, a tensioning cord 116 is introduced into the heart chamber through the left atrium and is directed through the mitral orifice to an anchored relation to the ventricular wall 34. Subsequent to the anchoring of the distal end, as at 18, the proximal portion and/or more specifically, the proximal end 116 Prime of the cord 116 threaded or otherwise connected to the base 56, receiving securing segment 72 and a remainder of the housing 50 such as through the aperture or slot 75 and the connecting linkage 74. Once the cord 116 and/or distal end 116" is connected in the manner described, the leaflet 100, which may be under the siege of prolapse, is disposed in a connecting orientation, within the interior of a capturing area 80 between the head portion 54 and the base 56 when in an open or at least partially open position. Hence, when the predetermined valve leaflet 100 is disposed in the connecting orientation, within the capturing area 80, the housing 52 or other appropriate portions thereof, such as end 53, are manipulated to force the positioning member or plunger 58 into driving relation to the head portion 54. This in turn will lower and/or dispose the first retaining segment 64 into engaging, gripping and or at least partially clamping relation to the predetermined valve leaflet 100. Further forced downward travel of the head portion 54, through activation of the plunger 58, will force the penetrating segment 70 of the securing member 68 into penetrating relation with the valve leaflet 100 and there through into connected, penetrating relation with the second or receiving segment 72, as clearly demonstrated in a comparison in the FIGS. 12 and 13. Once the securing member 68 is disposed in interconnecting relation between the proximal end 116" and the valve leaflet 100, as represented in FIG. 16, the securing assembly 50 will be operated or manipulated to facilitate the disposition of the head portion 54 into the open orientation relative to the base 56, as clearly represented in FIGS. 14 and 15. Once in the open position, the securing member 68 upon selective movement into the closed position, will be positioned in penetrating relation to the valve leaflet 100 and will thereby be disposed into the interconnecting relation between the valve leaflet 100, the proximal end 116" and the interconnected penetrating and receiving segments 70 and 72.

Therefore the interconnecting relation of the securing member 68 relative to the predetermined valve leaflet 100 will be such as to effectively grip and or sandwich it between the penetrating securing segment 70 and the receiving securing segment 72. As such, the distal end 116" of the cord 116 is also at least partially disposed in effectively connected relation with the penetrating segment 70 and receiving segment 72 as also clearly represented in FIGS. 15 and 16.

Figure 17:
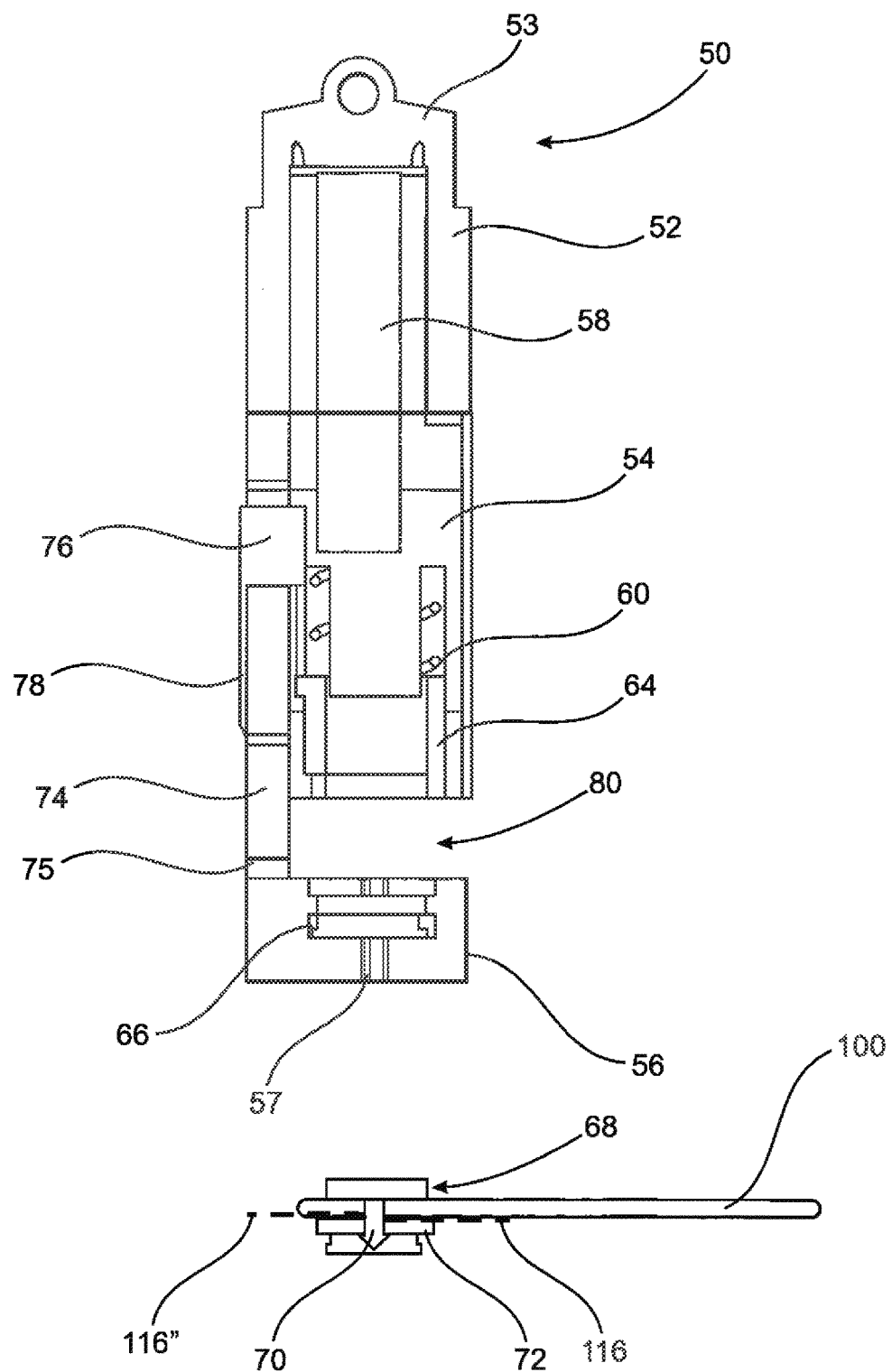
FIG. 17 is a schematic representation of another embodiment of the present invention similar to but distinguishable from the embodiment of FIGS. 10 through 16.

FIG. 17 represents yet another embodiment of the present invention, wherein the proximal portion of the chord 116 is connected to the valve leaflet 100 so as to apply adequate tension thereto by passing between the penetrating and receiving segment 70 and 72 respectively. As such, the distal end 116" of the cord 116 is not threaded through the receiving segment 72, as in the embodiment of FIG. 16, but is clamped, gripped and/or sandwiched between the penetrating and receiving segments 70 and 72 in interconnected, but not penetrating relation to the leaflet 100.

Figure 18:
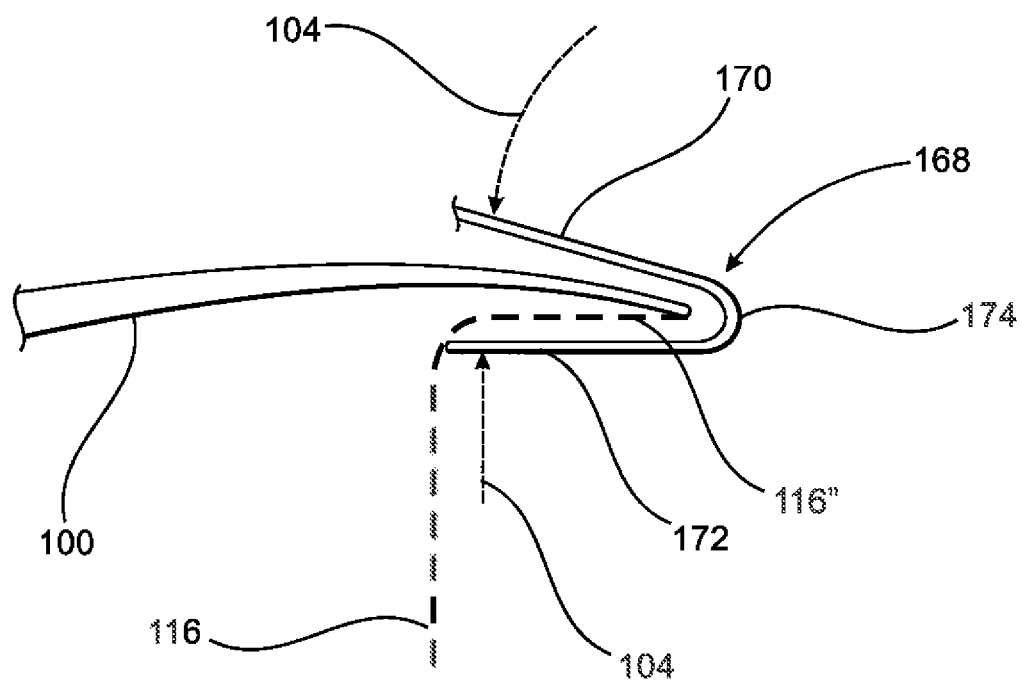
FIG. 18 is a schematic representation of another embodiment of the present invention similar to but distinguishable from the embodiment of FIGS. 10 through 16.

FIG. 18 schematically represents yet another embodiment of the securing member 168 comprising a clip-like structure including first segment 170 and a second segment 172 movably connected as by an integral connection and/or appropriate hinge portion 174. In this embodiment, the securing member 168 is operable to clamp the proximal end 116" of the proximal portion of the tensioning chord to the leaflet 100 as the proximal end is sandwiched between the first and second segments 170 and 172, when they are in a closed relation to one another and gripping or clamping engagement with the leaflet. Moreover, the material from which the securing member 168 is formed is structured to remain in the closed relation and gripping or clamping engagement with the leaflet 100 and proximal end 116", when a closing or gripping force is applied thereto as schematically represented by directional arrows 104.

In addition, the securing member 168 can be disposed in the aforementioned closed relation or gripping engagement relative to the leaflet 100 and proximal end 116" by the securing assembly 50, substantially as described above, with little or no structural or operational modifications be required.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. An instrument assembly for treating heart valve malfunction by securing a chord, pre-anchored at a distal end thereof to a heart, to a valve leaflet of the heart under sufficient tension to restrict prolapsing of the valve leaflet, said instrument assembly comprising;
   a securing assembly structured to dispose a securing member in interconnecting relation between a proximal portion of the chord and the valve leaflet,
   said securing assembly including a head portion and a base relatively disposable between open and closed positions and structured to retain said securing member in an operative position,
   said securing assembly structured to moveably retain said chord relative to said securing member, a position of said securing assembly relative to the distal end of the chord varying an operative length of the chord,
   a capturing area disposed between said head portion and said base, at least when said head portion and said base are in said open position,
   said capturing area configured to receive and removably retain the valve leaflet therein in a connecting orientation to said securing member, and
   said securing member being structured to penetrate and pass through the valve leaflet into said interconnecting relation between the chord and the valve leaflet when said head portion and said base are disposed into said closed position, and
   a severing member connected to and moveable with said securing assembly, said severing member disposable in severing relation to a proximal portion of the chord concurrent to disposition of said head portion and said base into said closed position and interconnection of said proximal portion of the chord with said securing member.

2. An instrument assembly as recited in claim 1 further comprising a positioning member movable with said head portion between said open and closed positions.

3. An instrument assembly as recited in claim 2 wherein said positioning member is connected to a housing and disposed in driving relation to said head portion when moving from said open position to said closed position.

4. An instrument assembly as recited in claim 2 further comprising a biasing structure disposed to normally bias said head portion from said open position to said closed position.

5. An instrument assembly as recited in claim 1 further comprising a retaining assembly disposed on both said head portion and said base and structured to removably retain the securing member in predetermined relation to the valve leaflet, at least prior to disposition of said securing member into said interconnecting relation.

6. An instrument assembly recited in claim 5 wherein said retaining assembly comprises a first retaining segment, disposed on the head portion and disposed and structured to removably retain and position a first securing segment into said closed position, and a second retaining segment, disposed on the base and disposed and structured to removably retain and position a second securing segment into said closed position.

7. An instrument assembly recited in claim 6 wherein at least one of said first and second retaining segments is structured to receive the chord in connected relation thereto and to a corresponding one of the first or second securing segments.

8. An instrument assembly recited in claim 6 wherein said first retaining segment is connected to said head portion and structured to position said first securing segment into said closed position; said second retaining segment connected to said base and structured to position said second securing segment into said closed position; wherein said first securing segment comprises a penetrating segment; and wherein said second securing segment comprises a receiving segment.

9. An instrument assembly recited in claim 8 wherein said penetrating segment is structured to be disposed in penetrating relation through the valve leaflet retained within said capturing area when the securing member is in said interconnecting relation.

10. An instrument assembly recited in claim 8 wherein said penetrating segment and said receiving segment are structured to be disposed in interconnecting relation to said chord and the valve leaflet when the securing member is in said interconnecting relation.

11. An instrument assembly recited in claim 8 wherein the chord is structured to be connected to the valve leaflet substantially between said penetrating and receiving segments when the securing member is in said interconnecting relation.

12. An instrument assembly for treating heart valve malfunction by securing a chord, that has a distal end thereof pre-anchored to a heart, to a valve leaflet under sufficient tension to restrict prolapsing of the valve leaflet, said instrument assembly comprising:
- a chord having a distal end disposable in anchored relation with a heart,
- a securing assembly structured to dispose a securing member in an interconnecting relation between a proximal portion of the chord and the valve leaflet,
- said securing assembly including a head portion and a base relatively disposable between open and closed positions and structured to removably retain said securing member in an operative position, said securing member being within said securing assembly prior to said securing member being disposed in said interconnecting relation,
- said securing assembly structured to moveably retain said chord relative to said securing member during positioning of said securing member, a position of said securing assembly relative to the distal end of the chord setting an operative length of the chord at the securing member,
- said base comprising a slot or aperture, the chord passing through the base via the slot or aperture for movably retaining said chord relative to said securing member during positioning of said securing member,
- a capturing area disposed between said head portion and said base, at least when said head portion and said base are in said open position,
- said capturing area configured to receive and removably retain the valve leaflet therein in a connecting orientation to said securing member, said securing member being structured to penetrate and pass through the valve leaflet into said interconnecting relation between the chord and the valve leaflet without varying said operative length of the chord set by said securing assembly when said head portion and said base are disposed into said closed position,
- a positioning member movable with said head portion between said open and closed positions,
- a connecting linkage mounted on the securing assembly, and structured for disposition of the positioning member and head portion between the open and closed positions,
- said connecting linkage comprising a partially slotted or apertured construction for movably retaining said chord relative to said securing member during positioning of said securing member.

* * * * *